(12) United States Patent
Taylor

(10) Patent No.: US 7,374,536 B1
(45) Date of Patent: May 20, 2008

(54) METHOD FOR ANALYSIS OF PAIN IMAGES

(76) Inventor: Colin R. Taylor, 196 E. 75 St., Apt. 18A, New York, NY (US) 10021

( * ) Notice: Subject to any disclaimer, the term of this patent is extended or adjusted under 35 U.S.C. 154(b) by 642 days.

(21) Appl. No.: 10/826,210

(22) Filed: Apr. 16, 2004

(51) Int. Cl.
*A61B 5/00* (2006.01)
*G01N 33/48* (2006.01)

(52) U.S. Cl. ............................. 600/300; 702/19

(58) Field of Classification Search ............. 600/300, 600/424, 427, 553; 382/128, 266, 293; 607/59–60; 702/19
See application file for complete search history.

(56) References Cited

U.S. PATENT DOCUMENTS

| | | | |
|---|---|---|---|
| 5,582,189 A | 12/1996 | Pannozzo | |
| 5,848,121 A | 12/1998 | Gupta | |
| 5,908,383 A | 6/1999 | Brynjestad | |
| 6,009,212 A | 12/1999 | Miller et al. | |
| 6,434,415 B1 | 8/2002 | Foley et al. | |
| 6,553,152 B1 | 4/2003 | Miller et al. | |
| 6,611,630 B1 | 8/2003 | Miller et al. | |
| 6,647,135 B2 | 11/2003 | Bonnefous | |
| 6,650,927 B1 | 11/2003 | Keider | |
| 6,653,947 B2 | 11/2003 | Dwyer et al. | |
| 6,654,642 B2 | 11/2003 | North et al. | |
| 6,656,695 B2 | 12/2003 | Berg et al. | |
| 6,697,535 B1 | 2/2004 | Dutta-Choudhury | |
| 2002/0030682 A1 | 3/2002 | Eberlein | |
| 2003/0139652 A1 | 7/2003 | Kang et al. | |
| 2003/0233053 A1 | 12/2003 | Woolf et al. | |

OTHER PUBLICATIONS

F. Bookstein et al, Comparing frontal cranial profiles in archaic and modern Homo by morphometric analysis, Anatomical Record (New Anat.) 1999;257:217-224.

Cerney et al, Image warping of three-dimensional body scan data, SAE Digital Human Modeling for Design and Engineering Conference 2003;Paper No. 2003-01-2231,Publ. SAE Internat.

Hood, Geometric Morphometric Approaches to the Study of Sexual Size Dimorphism in Mammals,Hystrix,(n.s.) 11 (1) (2000): 77-90.

*Primary Examiner*—Eric F. Winakur
*Assistant Examiner*—Michael Rozanski
(74) *Attorney, Agent, or Firm*—Leonard Cooper

(57) ABSTRACT

A method uses body images and computer hardware and software to collect and analyze clinical data in patients experiencing pain. Pain location information is obtained by the drawing of an outline of the pain on a paper copy or electronic display of the body image. Composite images are generated representing aggregate data for specified patient groups. The coordinates of common anatomic landmarks on differently designed body images are mapped to each other, permitting integrated analysis of pain data, e.g., pain shape, centroid, meta centroid, from multiple body image designs and display of all pain data on a single body image design. Differences and similarities between groups of patients are displayed visually and numerically, and are used to assign the probability of a given patient belonging to a particular diagnostic group or category of disease severity.

16 Claims, 20 Drawing Sheets

Unmarked Pain Diagram

Pain Diagram with Pain Markings

Pain Diagram with Computer-Identified Pain Shape

Centroid Mask – Right Anterior Shoulder

Centroid Mask – Lower Back

Close-Up of Lower Back Area showing individual pain centroids (closed circles) and the un-weighted meta-centroid (closed square)

Composite Figure of Pain Shapes from Lower Back

Striped Central Area encompasses approximately 50% of Pain Shape Outlines.
Dotted Outline encompasses approximately 80% of Pain Shape Outlines.

Examples of the Many Body Image Designs Used in Evaluation of Pain
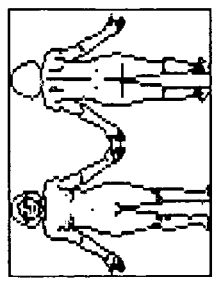
Fig. 20 a
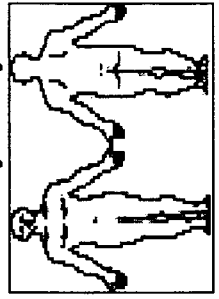
Fig. 20 b
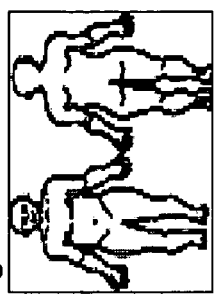
Fig. 20 c
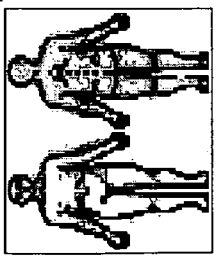
Fig. 20 d
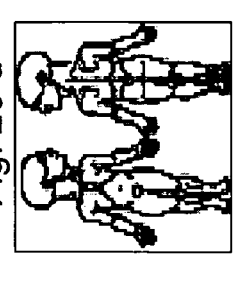
Fig. 20 e
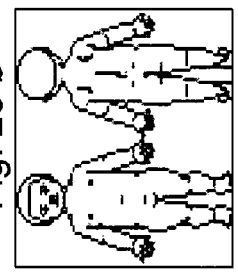
Fig. 20 f
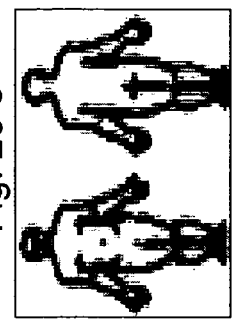
Fig. 20 g
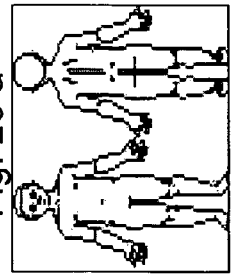
Fig. 20 h
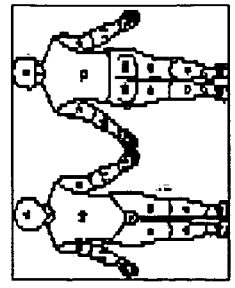
Fig. 20 i
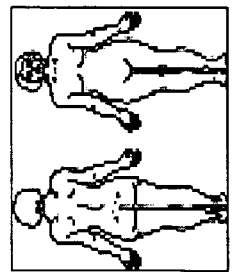
Fig. 20 j
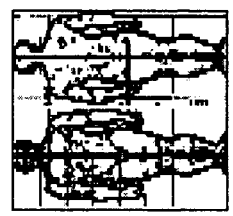
Fig. 20 k
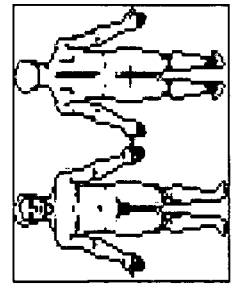
Fig. 20 l
Fig. 20 m
Fig. 20 n
Fig. 20 o

METHOD FOR ANALYSIS OF PAIN IMAGES

BACKGROUND OF THE INVENTION

The present invention relates to a method for recording and analyzing pain diagrams in which a patient or physician draws on a body image the location of pain suffered by the patient. Pain diagrams have been used for many years but are normally used merely for quick visual review to identify anatomic locations of pain.

Pain diagrams are routinely used in pain specialist offices and in clinical trials of pain therapy. Previous attempts to automate analysis of pain diagrams have been of limited value and have not provided detailed quantitative evaluation or been applicable to all of the many body image designs used in medical practice.

North et al ("Automated 'pain drawing' analysis by computer-controlled, patient-interactive neurological stimulation system", Pain. 1992 July; 50:51-7 and "Patient-interactive, computer-controlled neurological stimulation system: clinical efficacy in spinal cord stimulator adjustment, J Neurosurg. 1992 June; 76:967-72; also see U.S. Pat. No. 6,654,642) have used computer technology for direct recording by the patient of pain shapes. Using a pointing device and computer screen display, a patient with neurostimulation implants draws anatomic locations where pain is felt on a computerized body outline. The computer system adjusts the amount of electric pulse stimulation of the nerve so as to optimize pain relief. However, it does not provide diagnostic information or analysis of the paper pain diagrams used in ordinary clinical practice.

Other workers have divided the body image into a series of rectangles using a transparent grid; an observer then manually records which rectangles represent painful areas. These data may then be coded to computer files for analysis or analyzed manually. Using a grid system, larger areas of pain measured have been correlated with greater disease severity and poorer response to treatment. Thus, Toomingas ("Characteristics of pain drawings in the neck-shoulder region among the working population", Int Arch Occup Environ Health. 1999 March; 72(2):98-106) used an 878 pixel transparent grid to classify pain location in the neck-shoulder area. Total pain area, left-right distribution and symmetry were correlated with symptom chronicity and severity of disease. Takata and Hirotani ("Pain drawing in the evaluation of low back pain", Int Orthop. 1995; 19(6):361-6) used a grid system to show that patients with larger numbers of leg grid rectangles involved in pain showed poorer treatment outcomes. Similarly, Toomey et al ("Relationship of pain drawing scores to ratings of pain description and function", Clin J. Pain. 1991 December; 7:269-74) found that larger pain areas were related to increased disability in patients with chronic pain.

Digital subtraction is an established computer technique used in clinical medicine, e.g., for magnetic resonance visualization of blood vessels. It involves computer comparisons of pairs of pixels across two images. Normally, a baseline image is obtained prior to some intervention such as injection of a radio-opaque material into a blood vessel and compared with an image obtained after the injection. The idea of digital subtraction dates back to the 1930s, when the Dutch radiologist des Plantes produced subtraction images of contrast-filled vessels using plain film. From the "mask" image (i.e. the image of the object just before the contrast medium is injected) he produced a positive copy, onto which the images with contrast medium were overlaid to coincide, thus producing a subtraction image only displaying the contrast-filled vessels. Digital subtraction has not previously been used in analysis of pain diagrams.

The computer generation of composite images is an established technique used in medicine. For example, composite images are useful in integrating the data from multiple frames from a magnetic resonance image of the brain, using the techniques of coregistration (where images are superimposed on each other) followed by display on a composite image of the average intensity on a gray or color scale. Composite images have not been hitherto used for analysis of pain diagrams.

A further established computer technique, used in cartography, allows the user to "drill" up and down through different levels of detail in, for example, a map of the world. Thus, Internet sites such as mapquest.com allow the user to specify an address, say in New York City. The Internet site then displays a map at an intermediate level of detail and the user can click the "Zoom Out" or "Zoom In" button so as to display progressively larger geographical areas (with less detail) or progressively smaller geographical areas (with more detail, even to the level of individual streets and buildings). This technique has not previously been used to display different levels of anatomic detail in pain diagrams.

Since the late 1970s, workers in the field of comparative anatomy have used geometric morphometrics to compare the anatomic features of different groups of organisms. Geometric morphometric methods identify the location of selected anatomic landmarks and then apply techniques such as thin-plate spline transformation to warp an image by transforming input coordinates to output coordinates. Similarly, Gupta et al (U.S. Pat. No. 5,848,121) have described transformation of images in digital subtraction angiography using user-provided match points as the basis for interpolation techniques that correct mismatches between a mask and an opacified image. Such methods have not hitherto been applied to match pain diagrams of different designs.

PUBLICATIONS

Pain Diagrams/Drawings:

Arner M, Kopylov P, Holmberg J, "Pain drawing as an investigative tool in hand surgery", Scand J Plast Reconstr Surg Hand Surg. 1992; 26(3):271-4.

Andersson H I, Ejlertsson G, Leden I, Rosenberg C. "Chronic pain in a geographically defined general population: Studies of differences in age, gender, social class, and pain localization". Clin J Pain 9:174-182, 1993.

Benbadis S R, Herrera M, Orazi U., "Does the neurologist contribute to the care of patients with chronic back pain?" Eur Neurol. 2002; 48(2):61-4.

Bertilson B C, Grunnesjo M, Strender L E., "Reliability of clinical tests in the assessment of patients with neck/shoulder problems-impact of history". Spine. 2003 Oct. 1; 28(19):2222-31.

Bidaut-Russell M, Gabriel S E, Scott C G, Zinsmeister A R, Luthra H S, Yawn B., "Determinants of patient satisfaction in chronic illness". Arthritis Rheum. 2002 Oct. 15; 47(5):494-500.

Bolton J E, Christensen M N. "Back pain distribution patterns: relationship to subjective measures of pain severity and disability". J Manipulative Physiol Ther. 1994 May; 17(4):211-8.

Chan C W, Goldman S, Ilstrup D M, Kunselman A R, O'Neill P I, "The pain drawing and Waddell's nonorganic physical signs in chronic low-back pain", Spine. 1993 Oct. 1; 18(13):1717-22.

Dahl B, Gehrchen P M, Kiaer T, Blyme P, Tondevold E, Bendix T., "Nonorganic pain drawings are associated with low psychological scores on the preoperative SF-36 questionnaire in patients with chronic low back pain". Eur Spine J 2001; 10:211-4

Dzioba R B, Doxey N C. "A prospective investigation into the orthopaedic and psychologic predictors of outcome of first lumbar surgery following industrial injury". Spine. 1984 September; 9(6):614-23.

Elliott A M, Smith B H, Penny K I, Smith W C, Chambers W A., "The epidemiology of chronic pain in the community". Lancet. 1999 Oct. 9; 354(9186):1248-52.

Gallagher R M., "Primary care and pain medicine. A community solution to the public health problem of chronic pain". Med Clin North Am. 1999 May; 83(3):555-83, v.

Gilron I, Bailey J, Weaver D F, Houlden R L. "Patients' attitudes and prior treatments in neuropathic pain: a pilot study." Pain Res Manag. 2002 Winter; 7(4):199-203.

Gureje O, Simon G E, Von Korff M., "A cross-national study of the course of persistent pain in primary care". Pain. 2001 May; 92(1-2):195-200.

Haeri M, Asemani D, Gharibzadeh Sh., "Modeling of pain using artificial neural networks", J Theor Biol. 2003 Feb. 7; 220(3):277-84.

Hagg O, Fritzell P, Hedlund R, Moller H, Ekselius L, Nordwall A; "Swedish Lumbar Spine Study., Pain-drawing does not predict the outcome of fusion surgery for chronic low-back pain: a report from the Swedish Lumbar Spine Study". Eur Spine J. 2003 February; 12(1):2-11.

Hasselstrom J, Liu-Palmgren J, Rasjo-Wraak G., "Prevalence of pain in general practice"., Eur J. Pain. 2002; 6(5):375-85.

Jinks C, Jordan K, Ong B N, Croft P., "A brief screening tool for knee pain in primary care (KNEST). 2. Results from a survey in the general population aged 50 and over". Rheumatology (Oxford). 2003 Aug. 15

Knab J H, Wallace M S, Wagner R L, Tsoukatos J, Weinger MB., "The use of a computer-based decision support system facilitates primary care physicians' management of chronic pain". Anesth Analg. 2001 September; 93(3): 712-20.

Lindal E, Bergmann S, Thorlacius S, Stefansson J G, "The localization of pain in chronic fatigue syndrome on a pain drawing according to grid areas", Percept Mot Skills. 1996 October; 83(2):508-10

Loeser J D, Melzack R. "Pain: An overview". *Lancet* 353: 1607-1609, 1999.

Love A, Leboeuf C, Crisp T C, "Chiropractic chronic low back pain sufferers and self-report assessment methods. Part I. A reliability study of the Visual Analogue Scale, the Pain Drawing and the McGill Pain Questionnaire", J Manipulative Physiol Ther. 1989 February; 12(1):21-5.

MacFarlane B V, Wright A, O'Callaghan, Benson H A. "Chronic neuropathic pain and its control by drugs". Pharmacol Therapy 75: 1-19, 1997.

MacFarlane G J, Thomas E, Papageorgiou A C, Schollum J, Croft P R, Silman A J., "The natural history of chronic pain in the community: a better prognosis than in the clinic?" J Rheumatol 1996; 23:1617-20

Mann N H 3rd, Brown M D, Hertz D B, Enger I, Tompkins J., "Initial-impression diagnosis using low-back pain patient pain drawings". Spine. 1993 January; 18(1):41-53.

Margolis R B, Chibnall J T, Tait R C. "Test-retest reliability of the pain drawing instrument".Pain. 1988 April; 33(1): 49-51.

McBeth J, Macfarlane G J, Hunt I M, and Silman A J, "Risk factors for persistent chronic widespread pain: a community-based study", Rheumatology 2001; 40: 95-101

Milne J, Ongley M J, Klein R G, Dorman T A, Bjorn C., Lawrence E, Hubert J, "A new approach to the treatment of chronic low back pain", Lancet, july 18, 1987, pp. 143-146

North R B, Fowler K, Nigrin D J, Szymanski R., "Patient-interactive, computer-controlled neurological stimulation system: clinical efficacy in spinal cord stimulator adjustment"., J. Neurosurg. 1992 June; 76(6):967-72.

North R B, Nigrin D J, Fowler K R, Szymanski R E, Piantadosi S., "Automated 'pain drawing' analysis by computer-controlled, patient-interactive neurological stimulation system"., Pain. 1992 July; 50(1):51-7.

Ohlund C, Eek C, Palmbald S, Areskoug B, Nachemson A, "Quantified pain drawing in subacute low back pain. Validation in a nonselected outpatient industrial sample", Spine. 1996 May1; 21(9):1021-30

Ohnmeiss D D, "Repeatability of pain drawings in a low back pain population" Spine. 2000 Apr. 15; 25(8):980-8.

Ohnmeiss D D, Vanharanta H, Ekholm J "Relationship of pain drawings to invasive tests assessing intervertebral disc pathology", Eur Spine J.1999; 8(2):126-31

Ohnmeiss D D, Vanharanta H, Ekholm J. "Relation between pain location and disc pathology: a study of pain drawings and CT/discography". Clin J. Pain. 1999 September; 15(3):210-7.

Ohnmeiss D D, Vanharanta H, Estlander A M, Jamsen A., "The relationship of disability (Oswestry) and pain drawings to functional testing"., Eur Spine J. 2000 June; 9(3):208-12.

Parker H, Wood P L, Main C J, "The use of the pain drawing as a screening measure to predict psychological distress in chronic low back pain", Spine. 1995 Jan. 15; 20(2):236-43.

Pfingsten M, Baller M, Liebeck H, Strube J, Hildebrandt J, Schops P. "Psychometric properties of the pain drawing and the Ransford technique in patients with chronic low back pain" Schmerz. 2003 October; 17(5):332-40.

Rantanen P., "Physical measurements and questionnaires as diagnostic tools in chronic low back pain". J Rehabil Med. 2001 January; 33(1):31-5.

Reigo T, Tropp H, "Pain drawing evaluation—the problem with the clinically biased surgeon. Intra- and interobserver agreement in 50 cases related to clinical bias". Acta Orthop Scand. 1998 August; 69(4):408-11.

Rigby A S, Boswell R, Schollum J, Silman A., "The prevalence of chronic widespread pain in the general population"., J Rheumatol 1993; 20:710-3

Smith B H, Hopton J L, Chambers W A., "Chronic pain in primary care". Fam Pract. 1999 October; 16(5):475-82.

Szappanos L, Nagy Z, Papp T, "Use of the "pain drawing test" in the diagnosis of degenerative lumbal spinal stenosis", Magy Traumatol Ortop Kezseb Plasztikai Seb. 1994; 37(2): 169-74

Takata K, Hirotani H, "Pain drawing in the evaluation of low back pain", Int Orthop. 1995; 19(6):361-6.

Toomey T C, Mann J D, Abashian S, Thompson-Pope S, "Relationship of pain drawing scores to ratings of pain description and function", Clin J. Pain. 1991 December; 7(4):269-74.

Toomingas A., "Characteristics of pain drawings in the neck-shoulder region among the working population", Int Arch Occup Environ Health. 1999 March; 72(2):98-106.

Uden A & Landin L A "Pain drawing and myelography in sciatic pain", Clin Orthop 1987. 216: 124-130.

Vingard E, Mortimer M, Wiktorin C, Pemold R P T G, Fredriksson K, Nemeth G, Alfredsson L, Musculoskeletal Intervention Center-Norrtalje Study Group., "Seeking care for low back pain in the general population: a two-year follow-up study: results from the MUSIC-Norrtalje Study". Spine. 2002 Oct. 1; 27(19):2159-65.

Wincent A, Liden Y, Arner S, "Pain questionnaires in the analysis of long lasting (chronic) pain conditions", Eur J. Pain. 2003; 7(4):311-21.

Yap A U, Tan K B, Hoe J K, Yap R H, Jaffar J, "On-line computerized diagnosis of pain-related disability and psychological status of TMD patients: a pilot study", J Oral Rehabil. 2001 January; 28(1):78-87.

Geometric Morphometrics:

Bookstein, F L, Schafer K, Prossinger H, Seidler H, Fieder M, Stringer C, Weber G W, Arsuaga J-L, Slice D E, Rohlf F J, Recheis W, Mariam A J, and Marcus L F "Comparing frontal cranial profiles in archaic and modern Homo by morphometric analysis", Anatomical Record (New Anatomist) 1999; 257:217-224.

Cerney M M, Adams D C, and Vance J M "Image Warping of Three-Dimensional Body Scan Data", SAE Digital Human Modeling for Design and Engineering Conference. 2003; Paper No 2003-01-2231, Publisher SAE International.

Hood C S. "Geometric Morphometric Approaches to the Study of Sexual Size Dimorphism in Mammals", Hystrix, 2000; 11: 77-90.

Rohlf P J and Marcus L F, "A Revolution in Morphometrics", Trends in Ecology and Evolution. 1993; 8:129-132.

SUMMARY OF THE INVENTION

It is an object of the present invention to provide automated methods for recording and analyzing pain diagrams of human patients.

The patient (or another person such as a physician) is given instructions as to how to draw, on a human body image, the locations where the subjective sensation of pain is felt by the patient. A drawing device such as a pen is used to identify a continuous outline for each pain shape. This marked-up drawing is digitized and computer-coregistered with a non-marked-up drawing. The computer then performs a digital extraction procedure to automatically identify the pain shapes recorded by the patient. The computer automatically calculates a number of clinically relevant measures e.g. pain shapes, centroids and meta-centroids, derived from the pain location data and compares this dataset with a database derived from groups of patients, each group with a different diagnosis, a different level of disease severity or a difference in another clinical characteristic so as to assign the patient to one or more of these clinical groups or levels of disease severity. A computerized image is generated displaying the pain shapes for the patient together with other clinical data such as possible diagnoses or suggested therapies.

Aggregate pain displays for different patient groups are generated as composite images showing for each computer pixel location one of three displays: the proportion of patients with pain, the ratio of two types of pain, or an outline encompassing an absolute or parametric-statistics-based percentage of patients. Similarly, composite images can be generated for individual patients with multiple pain recordings.

Many different body image designs are used at different pharmaceutical companies and by different pain specialists, and the present invention provides the means to map each body image design to any other body design by identifying selected anatomic landmarks common to each body design as well as a digitized outline of the body outline. This permits comparison of data between different body image designs and display of all pain data from disparate designs in a single body image design. It also permits other types of mapping: between bilaterally symmetrical areas on the left and right of the body, between common points on the outlines of different views of the body (e.g., the front and the back), between a generic pain diagram suitable for patient groups and a patient-specific body image (e.g., based on a photograph of the body), between a scale of linked body images in which the nature and degree of anatomic detail varies (allowing a visual pain data display to drill up and down through different magnification scales and body image rotations so as to show the desired anatomic detail), and between recorded pain locations and the known body surface locations associated with disease of individual internal body organs.

The present invention also provides the means to differentiate between different types of pain information by using separate markings for each type, e.g., using separate color hues or intensities, or different symbols or hatching marks. Thus, for example, a human body image can be generated in which anatomic locations associated with nociceptive pain are shown in green, and locations associated with neuropathic pain are shown in blue.

BRIEF DESCRIPTION OF THE DRAWINGS

FIGS. 20 a-o show examples of the many different human body image designs used in the evaluation of pain, indicating the need for the process described in FIG. 18.

DESCRIPTION OF PREFERRED EMBODIMENTS

Figure 1:
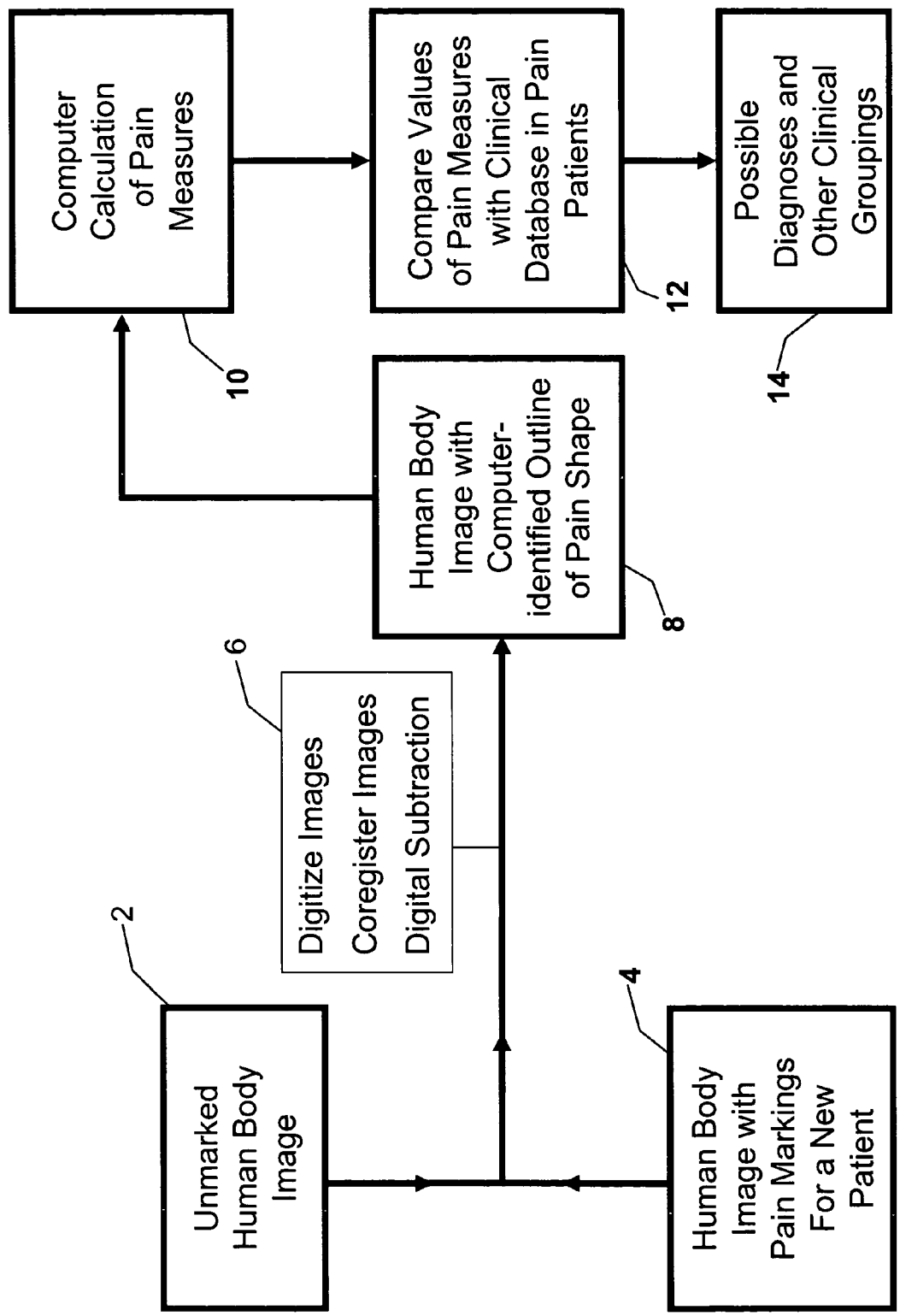
FIG. 1 is a flow chart illustrating the process in accordance with the invention of taking an unmarked body image and an image with pain markings and processing the images by computer to produce the outline of a pain shape together with suggested diagnoses or other clinical groupings.

The present invention relates to a method for recording and analyzing the locations where pain is experienced by a patient, as recorded by a patient or physician drawing on a body image.

Definitions of Key Terms:
- Affine Transformation: A mathematical transformation that is a combination of single transformations such as translation or rotation or reflection on an axis. In a typical affine transformation, given a matrix M, and a Vector V in homogeneous coordinates (e.g. V=(X Y 1)'), then V'=MV where V' is the new vector in the transformed space.
- Centroid and Meta-Centroid: As it applies to visual images, a centroid represents the mean position of the points making up a visual object. A meta-centroid is the point representing the mean position of a group of visual objects, and may be calculated as the mean position of the individual un-weighted centroids or as the mean position of all the points making up the group of visual objects.
- Composite Image: An image that is created by a combination of multiple images on a single sheet or display.
- Coregister: A process by which two or more images are spatially normalized with respect to one another. One such process uses fiducial points and linear transforms (translation, rotation, zoom and shear) so as to allow digital superimposition of common structures contained in the images.
- Digital Subtraction: A method for showing a selected element of an image without any interfering background. A first "mask" image (see "Image Masking" definition below) is compared with a second image obtained after display of the selected element. The computer digitally subtracts the first image data from the second image, leaving only the display of the selected element.
- Distance Map: A grey level image, where the value of each point of the foreground corresponds to its shortest distance to the background.
- Drill Up and Down: A technique usually performed by a computer, in which visual or non-visual data can be displayed at different levels of detail. Drilling up means that less detail is provided for any given object, whereas more objects can be displayed. Drilling down is the opposite.
- Ellipse: An oval figure, bounded by a regular curve, which corresponds to an oblique projection of a circle, or an oblique section of a cone through its opposite sides. The greatest diameter of the ellipse is the major axis, and the least diameter is the minor axis.
- Erosion Operators Erosion operators allow pixels on the outside of a shape to be discarded if they exceed preset values for the operators, causing "erosion" of the shape. Distance operators can use a recomputed distance map. Morphological operators compute the minimum and maximum pixel values within a certain scope.
- Fiducial: A point of reference, such as the center of a cross-hair in a visual image, used as a standard of reference of comparison and applicable to the process of coregistration.
- Geometric Morphometrics Geometric morphometrics represent a collection of approaches for the multivariate statistical analysis of Cartesian coordinate data, usually limited to landmark point locations. Kendall's shape space geometry (the estimation of mean shapes and the description of sample variation of shape using the geometry of Procrustes distance) is used.
- Image Mapping: The process whereby each pixel on one image is associated with (i.e., mapped to) a pixel on another image. As an example, the pixel at the center of the pupil of the right eye on a first image of a human body is associated with the pixel at the center of the pupil of the right eye on a second image of a human body.
- Image Masking: A cropping technique that uses a mask image to identify portions of an image that should be ignored ("masked") in subsequent analysis or display. Masking may use a separate coregistered image, or the image to be masked may itself contain the masking information. Optimally, masking is performed on a pixel-by-pixel basis, with each pixel being associated with a component that determines whether the pixel will be masked.
- Image Warping: A process whereby a Cartesian coordinate grid is applied to a reference image and the image and grid then distorted so as to match the reference image to a target image.
- Pain Diagram: A diagram or other image of a human body (normally of the front and back of the body) that is used as a guide in specifying the location of the patient's pain.
- Pain Drawing: A drawing of pain location made on a pain diagram. The term "pain drawing" is sometimes used interchangeably with "pain diagram".
- Pixel: The smallest discrete component of an image.
- Radial: A line radiating from a common center.
- RGB Color Coding: A coding system for three colors of light (Red, Green, Blue) that can be mixed to produce other colors. These colors correspond to the three color receptors in the human eye. Colored images are often stored on a computer as a sequence of RGB triplets (e.g., White=255,255,255; Black=0,0,0; Red=255,0,0; Green=0,255,0; Blue=0,0,255).

Thin-Plate Spline Interpolation: A thin-plate spline is the surface with minimum mean square second derivative energy that interpolates a given collection of points. Classical thin-plate spline techniques (or simple extensions of these techniques) can be used to map common locations between different images for which a number of common landmarks have already been identified.

Pain diagrams (also known as pain drawings) have been used by physicians for at least 40 years to identify pain location. Although they are clinically useful, the lack of a method for extracting and analyzing the pain location information has prevented their being used to full advantage. Frederick Wolfe (J Rheumatol 2003; 30:369-78) has stated that pain diagrams " . . . are difficult and time consuming to score" but that "clinicians can get a quick and useful picture of a patient's pain by just looking at a drawing . . . "

Several previous attempts have been made to computerize pain diagrams but these have not resulted in their common use in ordinary medical practice. No workers have developed an automated, quantitative, diagnostic method for analyzing pain location data drawn on pain diagrams. In addition, pain diagrams of many different designs are used by pain specialists and pharmaceutical companies around the world, so that any method and system to analyze all such data would have to work effectively for each of these many body image designs.

Computer Identification of Pain Shape Markings on a Human Body Image

The present invention digitizes a body image on which the pain locations for a patient have been recorded, compares the resulting digitized image to a digitized image of an unmarked body image (on which no pain locations have been recorded), and automatically determines pain locations by digitally subtracting, on a pixel-by-pixel basis, the data on the unmarked image from that on the patient-drawn image. All images use common fiducial points on the image to coregister all images to the same coordinate space (using an affine transformation comprising a combination of the single transformations of translation, rotation, shear and scale). The pain locations for each patient are then compared with a database containing patients in various clinical groups (e.g., based on diagnosis, pain type or disease severity) and patients are allocated to one or more clinical groups.

Automated identification of pain shapes can be performed for any of the many varieties of body image designs used in the medical community. Thus, the digital subtraction process is based on a digitized image of an unmarked copy of the particular body image design being used.

In the present invention, a computer automatically detects each pain shape drawn and calculates a number of data items related to the pain shape, including the size (calculated area), centroid, outline, shape type, and anatomic areas occupied by the pain. In addition, computationally and analytically simpler surrogates of certain measures may be used. For example, most pain shapes are approximately elliptical in shape and the pain outline can be conveniently approximated by calculating an ellipse derived from the long and short axes of the pain shapes; ellipsoid data is simpler to analyze when aggregating data from groups of patients.

It is well known to those skilled in the art that the location of pain in the body is closely related to the underlying diagnosis. Thus, pain in the lower back, the knee, the shoulder, or the hip is most commonly associated with degenerative disease of the structures in those locations (joints, inter-vertebral disks, cartilage, bursae, tendons, etc.); these types of pain are termed "nociceptive". In contrast, pain in the leg in the distribution of the L5 or S1 nerves is likely to be caused by sciatica related to irritation of those nerves as they exit the spine; similarly, bilateral generalized pain in the feet and lower legs is commonly caused by peripheral neuropathy; these types of pain are termed "neuropathic". However, no systematic studies have hitherto been performed that precisely identify the distribution of pain in these conditions. The systematic, quantitative collection of data made possible by the present invention remedies this defect.

Statistical analysis of pain shape data is used to identify the pain patterns that differentiate different patient groups, for example, groups identified by diagnosis, disease severity or other clinical variables. The pain shape of an individual patient can then be compared with these pain patterns, allowing assessment of the probability of the patient belonging to a particular diagnostic or other grouping.

Various statistical techniques may be used to identify pain patterns. One technique is to use the centroid of a pain shape and the calculated area of a pain shape, two variables that effectively differentiate between pain patterns associated with different diagnoses. Thus, the location of the centroid for a given patient can be compared statistically with the locations for the centroids associated with each particular diagnosis, and a list of diagnoses in order of probability generated. For diagnostic categories that may overlap in centroid location, inclusion of the size of the pain shape may differentiate between these overlapping categories. Thus, pain involving the knee may be localized (and usually representative of local knee disease) or more generally distributed above and below the knee (for example in some patients with sciatica); these two types of patients may be easily differentiated by measures of the size of the pain shape (such as the calculated pain area or the length of the vertical axis of the pain shape). Similarly, neuropathic pain can be differentiated from nociceptive pain not only by the location of the centroid but also by the total calculated pain area (which is normally of larger size in neuropathic pain). An alternative approach is to use the generalized Hausdorff measure (a means of determining the resemblance of one point set to another, by examining the fraction of points in one set that lie near points in the other set) to calculate the closeness of a given patient's pain shape to the group pain shape associated with a particular diagnosis. In addition to determining the pain patterns of groups for which the members are already known (e.g., patients with localized nociceptive knee pain), data-driven clusters of patients with particular pain patterns may be identified using the technique of cluster analysis which generates a dendrogram (tree diagram). Selection of the number of clusters to retain in a cluster analysis can be determined by replicating the analysis in separate datasets or in data subsets, and by determining which clusters reflect clinical realities. Such factor analysis can provide insights across or within clinical groupings.

The basic methodology described above may be enhanced by the following refinements:

Display Of Digitized Human Body Image On Computer Monitor for Production of Pain Markings Hard copies of pain diagrams are normally used and these may be digitized after the pain shapes have been recorded. However, a patient or physician may also interact with a computer, display monitor and pointing device to record pain information, rather than drawing pain shapes on a hard copy. Personal details such as age, sex, height, weight, ethnic group, and build are entered, and this information can be used to bring up a body image that is the closest match to the patient's own body. A pointing device such as a mouse is then used to draw the shapes of pain on the body image. The patient may also indicate, using a designated signal such as a mouse click, the point where the pain is worst.

Where the pain shape is recorded by direct interaction with the computer, the computer can "drill down" to the areas of pain, presenting a more detailed view with anatomical structures labeled, and superimposing the pain shape already identified. This allows the pain shape to be edited to provide more precise anatomic detail. Additional views can be displayed in the drilled-down presentation (for example, a patient indicating pain on the medial side of the right knee in an anterior view can be shown an additional view that shows the right knee from the medial aspect and not just from the anterior and posterior aspects of the knee). The computer can then drill back up to the full body image with a more accurate picture of the pain shapes.

Fitting of Patient Pain Pattern to Predetermined Pain Patterns

In a further approach, the patient is asked if the pain location fits one of several predetermined pain locations identified from pain patterns seen in a large group of pain patients. Since pain shape centroids provide stable measures of pain location, a particularly valuable application of this approach is to ask the patient if the center of the pain is located inside a visually displayed predetermined pain location. Normally, to avoid influencing the patient excessively, this approach may be applied after the original pain drawing has been obtained in an unbiased manner. For example, this approach may facilitate categorization of the patient's pain into one of several types of knee pain (such as femoropatellar syndrome, injury of the medial meniscus or medial ligament, injury of the lateral meniscus or lateral ligament, prepatellar bursitis, anserine bursitis, or Baker's cyst).

Visual Summary of Pain Locations and Clinical Features

After the pain shapes have been delineated, a computerized image can be generated for each patient showing the pain shapes, together with a listing of possible diagnoses or other clinical characteristics associated with the pain locations. The patient or physician can be provided with a computer monitor display or hard copy (combining graphics and text) that specifies possible diagnoses based on the pain distribution pattern described by groups of patients with known pain specialist diagnoses and completed pain diagrams. Any of many types of coding system can be used to designate the nature of the clinical information to be displayed. This can include textual descriptions (which can be visually linked to a pain location by an arrow), and various identifying markers (such as color hues or intensities, a gray scale, black and white hatching, or stippling) for a body location or pain shape together with a coding key that matches the marker with a textual description of its meaning.

Body-Area-Specific Masks

Since painful areas of different etiology can occur in different body locations, a mask image can be used to identify those pain shapes for which the centroid is present inside a predefined portion of the body image. For example, if the area of interest is the lower back, each pain shape can be reviewed to identify if the centroid of the pain shape is contained within a body image mask confined to an area of the lower back typically associated with the centroids of pain shapes from other lower back pain patients. The mask is coregistered with the image containing the pain data. A computer program can apply several different masks, each evaluating pain in a particular body location.

Use of Both Visible and Palpable Anatomic Landmarks

Most anatomic landmarks in human body images represent locations that can be identified by visual inspection of a human body. However, a further method of the present invention uses anatomic landmarks that may not be visible but which the person recording the pain shape can feel. This is particularly useful for anatomic areas where the patient himself finds it difficult to confirm location by visual inspection, for example on the back of the body, or in obese patients where fat may obscure common landmarks. An example is the lower back where the bony protuberances of the posterior iliac spine, the L4/L5 vertebral spines, and the upper edge of the sacrum can be identified by the physician and perhaps by the patient also.

The different types of anatomic landmarks can be associated with different methods of visual display. The level of detail in different portions of a body image may be adjusted so as to reflect medical importance and disease frequency. For example, the head, lower back, knee, shoulder, hip and foot areas are common anatomic areas of pain and it is useful for the body image to emphasize visual or palpable anatomic landmarks in these areas. Dotted lines or lines of different width or shading and the techniques of non-photorealistic rendering may be used to focus the attention of the person recording the pain shape on certain anatomic features in areas commonly associated with pain (e.g., bony protuberances that can be felt on the outside of the body, and other structures underneath the body surface). The curvature of the body outline can also be enhanced in such areas as a means of emphasizing these features. Instructions to the pain recording person are given and include means for location of each landmark.

Centroids as Stable Markers of Pain Location

Pain shapes drawn on a body image tend to be of many different sizes and contours. However, the calculated centroid (the mean position of the points making up the pain shape) provides a stable marker of pain location. Thus, the outlines of shoulder pain shapes may be very variable, but the centroids for such pain shapes tend to be closely clustered in a small anatomic area. Mathematical techniques such as cluster analysis may be applied to a group of centroids to identify data-driven local peaks representing anatomical concentrations of pain ("pain clusters"). A more powerful separation of patient groups may be obtained by combining centroid data with other data. For example, patients with nociceptive pain tend to have small, localized areas of pain whereas patients with neuropathic disease tend to have larger pain shapes—a finding that has both diagnostic value and possible implications for the underlying pathogenesis of pain in nociceptive and neuropathic disease. Special analysis, for example incorporating both centroid location and the major and minor axes of the fitted centroids, may allow separation into primarily neuropathic and primarily nociceptive pain types even where the centroids overlap.

Computer Differentiation of Background and Pain Markings by Use of Different Colors A further method facilitates computer differentiation between the underlying body image outline and the patient's drawing by using one color (e.g., cyan) for the background diagram and another color (e.g., markings from a black pen) for the patient's drawing. The essential requirement for this approach is for the two colors to be distinguishable in at least one of the three constituent RGB colors. In the case of cyan and black, for example, the RGB signatures are 0, 255, 255 (cyan) and 0, 0, 0 (black). Thus, with appropriately chosen threshold levels for the various color channels, the computer can distinguish regions of the images that contain the original body image markings (i.e., prior to addition of any pain markings), the patient's pain markings, both or neither.

Editing of Pain Markings Prior to Computer Measurement of Pain Shape

One of the purposes of the present invention is to analyze pain diagrams that exist in the files of many different pharmaceutical companies and pain specialist offices. These legacy pain diagrams share two analysis problems:

The first problem is to map the many different body image designs to each other or a common body image design—this problem is solved by the mapping methods used in the present invention.

The second problem is that many different methods, and different instructions for those drawing the pain shapes, may have been used for recording the pain shapes—and this problem is addressed by human or computer editing that transform the pain markings into pain shape outlines that can be read using a computer-based analysis procedure.

The first step in addressing the second problem is to identify the pain markings automatically using the coregistered images and digital subtraction procedure described above.

The second step is to determine whether or not such pain markings on a specific body image represent a single pain shape with a continuous outline—in which case, analysis can proceed without editing of the pain markings.

The third step, for patients with more than one pain shape identified, is to determine whether some or all of the multiple pain shapes can properly be combined as a single pain shape. There are two legitimate ways of performing this combining step—a human review method, and a computer method. In the human review method, a trained, unbiased observer (who is unaware of the clinical features of the patient, such as diagnosis or treatment assignment) evaluates the pain markings and draws the edited outline of a pain shape or outlines of multiple pain shapes (on a paper copy that is subsequently digitized, or on a computer screen using a marking device). In the computer method, a set of computer algorithms that evaluate factors such as the type of markings (e.g., hatched or stippled), the distance between nearby pain shapes, and correspondence to established pain patterns in other patients, is applied to perform a similar combining function. Using either method, it may also be determined that no valid pain shape data are available in a given pain diagram for a given data analysis.

Both human and computer editing of pain markings should apply similar methods that depend on the nature of the deficiencies in pain markings. One common deficiency is that the pain shape is indicated by hatching or stippling rather than a single continuous outline—this can normally be remedied by human or computer drawing of an outline that encompasses all the hatching or stippled elements—the same procedure being used for all pain markings to be included in a particular data analysis. A second common deficiency is that an arrow is drawn to a particular body area but no indication of the extent of the pain shape is provided—in such cases, the pain can be assigned to one of a set of predetermined body areas, but no analysis involving the size of the pain shape can be performed.

A key consideration in valid human editing of pain markings is that the process be consistent and unbiased—it is essential that the human editors be trained in consistent application of the editing procedures and that no clinical details or drug assignments are provided to bias the editing procedure. In the case of computer editing, no single algorithm is likely to be suitable for editing all pain markings—rather, a preliminary (human or computer) assessment should be made as to what particular defect in pain recording is present, and then the appropriate computer algorithm applied. It may also be appropriate to have unbiased human review of the computer-determined pain outlines to detect cases where the computer procedure clearly did not work effectively.

In all clinical studies, the same recording instructions are likely to have been given for all patients, regardless of treatment group. Accordingly, it will normally be possible to perform an unedited and unbiased analysis of the pain markings, even in patient groups for which inferior pain recording methods were used; thus, some analysis and inter-group comparison should be feasible and clinically useful—e.g., generation of a composite image with color intensity based on the numbers of patients in the group with pain at a given pixel. However, in some cases the quality of the pain markings may be so poor that neither a human observer nor a computer algorithm can reliably determine a pain shape outline, and such diagrams should not be subjected to any analysis that requires a pain shape outline.

Pain Diagnosis by Combination of Pain Location and Pain Quality Data

Although the pain location information by itself is a powerful aid to diagnosis, even greater diagnostic precision may be obtained by combining pain location information with other clinical data on the patient, e.g., information about the quality of the symptoms experienced by the patient. Thus, it is well known to those skilled in the art that neuropathic pain is associated with sensations such as numbness, pins and needles, a feeling like electrical shocks, a hot/burning feeling, or worsening of the pain with light touching. Thus, a diagnosis of neuropathic pain can be more accurately identified if pain location and pain quality data are combined. Since many patients have several different locations containing pain shapes, and these pain shapes may be related to different medical conditions, it is important to ensure that the pain quality data collection is specifically focused on pain in individual locations.

Recording of Pain Markings on Photograph of Actual Patient with Pain

Traditionally, pain drawings have used generic unisex diagrams of the human body that do not take into account individual features of a given patient. The shape of the human body is very variable from individual to individual, depending on such factors as age, sex, ethnic background, body build, and obesity. All such factors can be taken into account by using a photograph of the actual patient suffering pain, on which photograph the patient can mark the actual locations of pain. These pain markings can be transferred to a mapped generic human body image for inclusion in analysis of similarities and differences from pain markings of other patients. With the widespread availability of digital cameras, digitized photographs are easy to produce (and may optionally be edited to identify relevant anatomic landmarks). Since a patient may more easily record pain shapes on an image of his or her own body, accurate recording is facilitated. Use of photographs is particularly suitable where a single patient records pain on large numbers of occasions, thus justifying preparation of a patient-specific blank body image.

Composite Images and Aggregate Analyses of Pain Characteristics for Patient Groups The present invention can generate a composite image for one or more patient groups that displays the pain location for the group as a whole.

A composite image can be generated in several ways, all of which require a coding system that relates a given identifying marker to a given clinical characteristic. Display of identifying marker data may use different color hues or intensities, or different monochrome patterns. In addition, textual descriptions can relate specified groups of pixels to clinical characteristics.

Such approaches can use before-and-after composite images to provide a visual demonstration of the efficacy of a particular treatment suitable, for example, for marketing use by pharmaceutical companies. For many years, pharmaceutical companies developing medications to control pain have used pain diagrams in their clinical trials. Using the present invention, these pain diagram data from clinical trials are now accessible to formal, quantitative analysis that could provide important marketing or medical uses—such as before-and-after composite images in drug and placebo treatment groups, or identification of probable responders to drug therapy (as a function of variables derived from a baseline pain shape). In addition, important insights into the distribution patterns of clinical pain may be achieved since the data in all the disparate body image designs used in different clinical trials can be transformed into comparable data in a single generic body image design. For complex composite images, explanatory text (optionally color-coded) can be added. A composite image may also be generated to show the different body locations associated with two or more different characteristics—e.g., nociceptive and neuropathic pain.

Smoothing of Composite Image by Parametric Statistics

The present invention can also generate composite images using parametric statistics and statistical probabilities (rather than actual raw data). Images can be created that show a smooth gradation in intensity of the composite image from the center of a pain location (say the lower back) to the periphery of the pain location.

Each pain shape for a given patient has an outline indicating the outside of the pain shape. In the present invention, instead of plotting the color intensity for a pixel purely as a function of the number of patients in the group whose pain is present at a particular pixel, a separate composite image may be generated where the color intensity (or some other visual variable) represents the statistical probability of a given patient in the group having pain present at that pixel. This approach supplements the discontinuous, patchy composite image based on the actual number of patients with pain at that pixel with the statistical probability of a patient in the group having pain at that pixel, resulting in a continuous gradation of color or gray scale intensity and a better representation of the underlying distribution of pain. In one approach, the value of the visual variable may be a function of the distance from the group meta-centroid with the visual display being based on such standard statistical values as the mean, standard deviation, and standard error of the mean.

A number of reservations should be applied in evaluating this parametric statistics approach:

It applies certain simplifying statistical assumptions, such as calculation of the normal (Gaussian) distribution around the meta-centroid. Most biological data have an approximately normal distribution and perform in accordance with the Central Limit Theorem. However, is may sometimes be appropriate to apply tests for normality (e.g., the Pearson and Kolmogorov-Smirnov tests) to determine the degree to which the dataset comes from a normally distributed population.

Certain composite images may be confined to certain body areas, so that pain shapes are artificially truncated at the edge of the body area mask that is used. An example is where a patient may have both nociceptive low back pain and neuropathic sciatica and it is desired to separate these two pains by creating a back pain mask and a sciatica mask with the dividing line being the posterior iliac spine and superior edge of the sacrum.

Separate sets of parametric statistics are calculated for each radial around the meta-centroid. A statistical value for a particular radial (such as the mean distance+1 standard deviation which for an individual radial encompasses about 80% of observations) has a discrete probability of an outline lying inside the statistical value. However, it is less simple to calculate the probability of any portion of a pain shape lying inside a parametric statistics-based outline derived from a combination of data on all radials.

Importantly, the purpose of this approach is to assist the physician in deciding if the location of the pain shape outline in a particular patient is consistent with a particular diagnosis and inconsistent with other diagnoses. This requires knowledge of the relevant sensitivity (for detecting patients with such a diagnosis) and specificity (for excluding patients with other diagnosis). This will vary from diagnosis to diagnosis and can only be determined by acquisition of pain shape data on an adequate number of patients with and without the diagnosis. However, for the first time, the method of the present invention provides a means of acquiring the quantitative information required to make these determinations.

Integration of Pain Data from Body Images of Different Design

A further method allows interchange of data and visual displays between disparate body image designs.

The coordinates of selected common anatomic landmarks on the outline of the body image or within this outline are recorded for each body image design using user identification by a pointing device (this method being optionally supplemented by computer-assisted identification of landmarks). For most anatomic locations, a landmark is best identified by the user clicking with a pointing device at the anatomic location. In some such cases, the computer can refine the user's approximate estimate of anatomic location, e.g., where the user clicks on a body curve on the outline of the body and the computer finds the point in that general area that represents the maximum curve of the body outline. This approach may optionally be used to identify, for example, the tip of the shoulder, the most distal point on each of the fingers and toes, the centroid of the eye outline, or the centroid of the mouth shape. For some anatomic landmarks, computer identification alone may be more reliable than manual identification, e.g., the vertical line in the middle that evenly divides a body image into left and right sides of the body, or the top of the head.

Using common landmarks that lie along the outline of the body images, each pixel along the entire body outline in one body image design is mapped to the corresponding pixel in the other body image design. Such outline mapping may be performed in several ways, for example, on the basis of the relative distance between the two anatomic landmarks on either side of the pixels, or using the method of Bookstein et al ("Comparing frontal cranial profiles in archaic and modern Homo by morphometric analysis", Anatomical Record: New Anatomist, 1999; 257:217-224) in which outline landmark points are mathematically slid along the outline curve until they match as well as possible the positions of the corresponding points along an outline in a reference specimen; these outline landmarks are constrained to retain their relative position on the outline curve. Specific mapping of outline landmarks ensures that each pain shape point mapped to a second human body image design will lie within the body image.

In addition, using selected pixels from the mapped outlines of the body images of the two designs, optionally together with any common anatomic landmarks in the interior of the body images of the two designs, each pixel in the interior of the body image of one of the designs is mapped to a pixel in the interior of the body image of the other design. The method of thin-plate spline interpolation or variants thereof with warping of the respective spaces of the two designs may be used to superimpose the common elements of the two designs.

The two body image designs can be superimposed on a computer monitor display, with each being displayed in its own warped space. The user can then add, reposition and delete landmarks until the best possible spatial mapping between the common elements of the two designs has been obtained.

Many pain diagram designs used by pharmaceutical companies or pain specialists are not optimally designed—for example, the diagrams may not provide enough anatomic detail to link the pain shape to the anatomic location or underlying structure, or may not be bilaterally symmetrical. Transfer of the pain data to a more optimally designed body image design may disclose additional useful information.

In addition, transfer of data from disparate body image designs to a single optimum body design can allow comparison of pain diagram data obtained in clinical studies of different design. This allows combined analysis of therapeutic or diagnostic pain data from different clinical studies. These mapping techniques may be supplemented by additional methods to achieve the following:

Transfer of Recorded Pain Data Between a Generic Body Image and a Patient-Specific Body Image A further method transfers pain data collected using a generic body image to the same anatomic areas on a photograph specific to the patient whose pain is being recorded. In like manner, data recorded on a patient-specific photograph-based pain diagram can be transferred to a generic pain diagram for analysis of group data.

Transfer of Recorded Pain Data Between a Generic Body Image and a Demographic-Based Body Image A further method transfers pain data collected using a generic body image to the same anatomic areas on a body image specific to the demographic group to which the patient belongs (e.g., according to age, sex, ethnic group, or body size). In like manner, data recorded on a demographic-based body image can be transferred to a generic body image for analysis of group data.

Linked Scale of Pain Diagrams with Different Levels of Anatomic Detail

A further method involves the design of a linked scale of pain diagrams with different levels of anatomic detail, each coregistered with the others, so that the user can drill up or drill down through the diagrams to record and display data at the desired level of detail and emphasis.

Mapping of External Body Surface to Internal Body Structures

A further method maps the external surface of the body to internal body structures, providing additional information of possible diagnostic value. For example, pain in the body surface area overlying the kidneys may suggest urinary infection. However, since body structures may migrate during the embryonic stage, pain originating from a particular organ such as the heart may not necessarily be located in the skin over the organ. Thus, mapping to the external body surface must take into account the typical locations for pain originating from particular organs.

Integrated Analysis of Left- and Right-Sided Body Pain

The human body is in large part bilaterally symmetrical and it is sometimes clinically useful to combine or compare information from both sides of the body; this can be achieved in the present invention which allows mapping of the left and right sides of the body to each other. For example, a patient may have pain in both knees but the actual location of the knee pain may differ between the knees. Similarly, in a clinical study of a new drug, it may be useful to transform left-sided sciatica data into right-sided sciatica data, thus increasing the sample size available for analysis of the drug's effects on sciatica pain.

Contiguous Pain Shapes in Different Body Views

A further method maps the front and back of the body image using common anatomic landmarks seen from both front and back. This allows application of an algorithm that determines if there is a single contiguous pain shape (e.g., on the front and back of the left shoulder, allowing integrated analysis of the entire left shoulder).

Referring to the drawings, FIG. 1 is a flow chart showing an unmarked human body image 2 and a human body image with pain markings 4. These two images are digitized and coregistered, and digital subtraction is performed 6 to produce a digitized human body image containing a computer-identified pain outline 8.

Computer identification of the pain shape outline is performed using the following steps:

a) Set a threshold value for a pixel variable that allows differentiation between the human body image and the drawn pain shape:
   Threshold the patient drawn image to determine a set of pixels that were actually drawn on to indicate areas of pain.
b) Calculate the distance map for the image:
   Calculate the distance map (a grey level image where the value of each point of the foreground corresponds to its shortest distance to the background) for the image from step a) where the drawn pixels are at distance = 0.
c) Set a threshold for distance map values within which pixels will be provisionally considered part of the same pain shape:
   Threshold on distance the image from step b) all pixels which are less than a preset threshold.
d) Starting at the outer border of the provisional pain shape, discard pixels that exceed preset values for erosion operators:
   Erode the image from step c) using either distance based or morphological based erosion operators.

This pain outline is then analyzed 10 by computer to calculate various pain measures including the calculated area occupied by the pain shape, the center of the pain shape, and the anatomic location involved. The values of these pain measures are then compared 12 with those in a database of pain patients with various known clinical characteristics, and possible diagnoses and other clinical groupings 14 may be produced for the patient.

Figure 2:
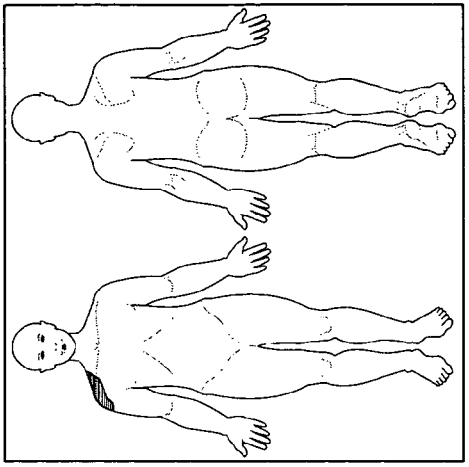
FIGS. 2 a-e shows examples of an unmarked pain diagram, a diagram with a patient's pain markings, and a diagram with a computer-generated pain shape, generated according to the process in FIG. 1.
Figure 2:
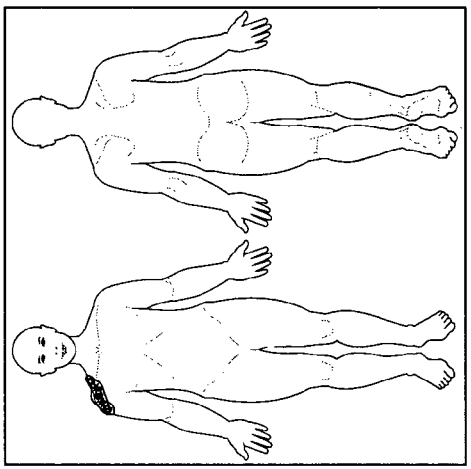
Figure 2:
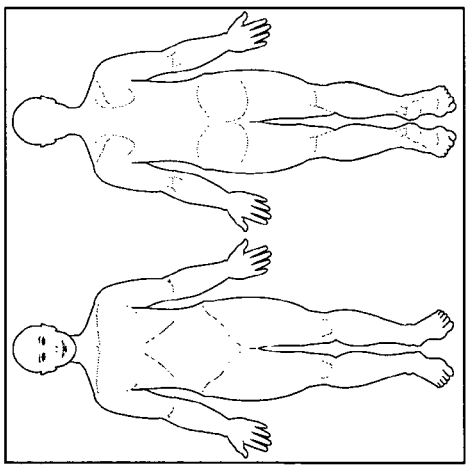
Figure 2:
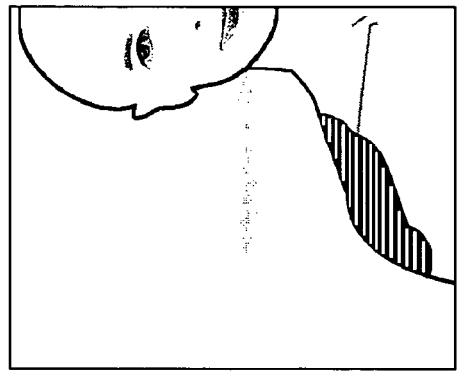
Figure 2:
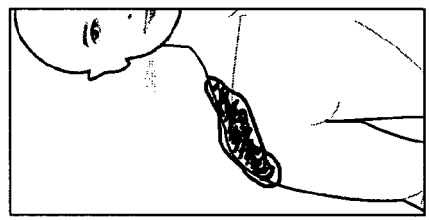

FIGS. 2a-e show examples of body images, generated according to the process in FIG. 1. FIG. 2a shows an unmarked body image. FIG. 2b shows a patient's right anterior shoulder pain markings (a magnified portion of which is shown in FIG. 2d). FIG. 2c shows a computer-identified shoulder pain shape (a magnified portion of which is shown in FIG. 2e).

Figure 3:
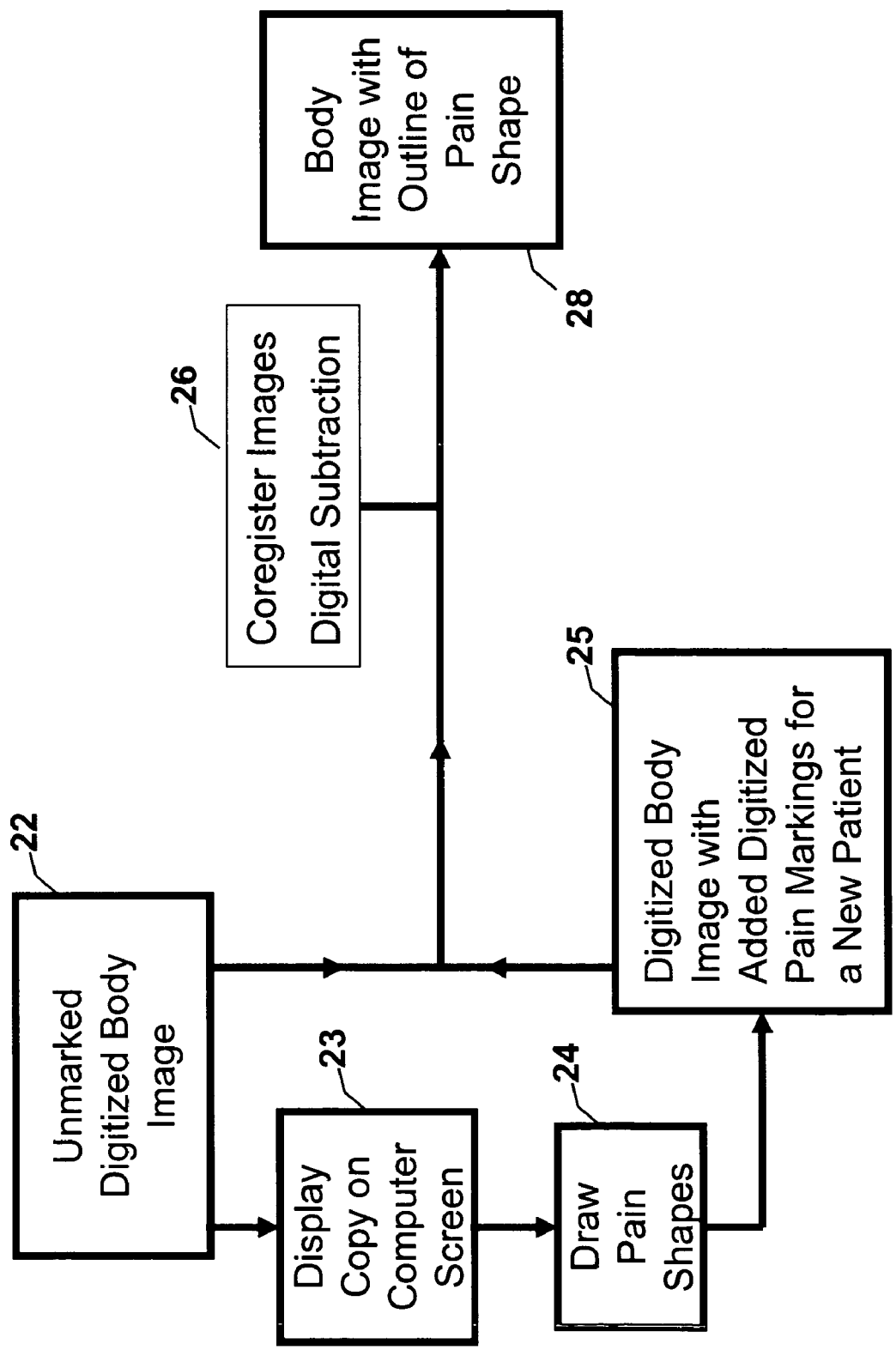
FIG. 3 is a flow chart in which a computer monitor display and previously digitized versions of body images are used to perform the processes described in FIG. 1.

FIG. 3 is a flow chart in which a digitized unmarked human body image 22 is displayed 23 on a computer screen and a patient's pain is electronically drawn 24 on this image resulting in a digitized human body image 25 with pain markings. The body images 22 and 25 are coregistered and digital subtraction is performed 26, resulting in a digitized body image 28 containing a computer-identified pain outline. This image is then processed as in steps 10, 12 and 14 of FIG. 1.

Figure 4:
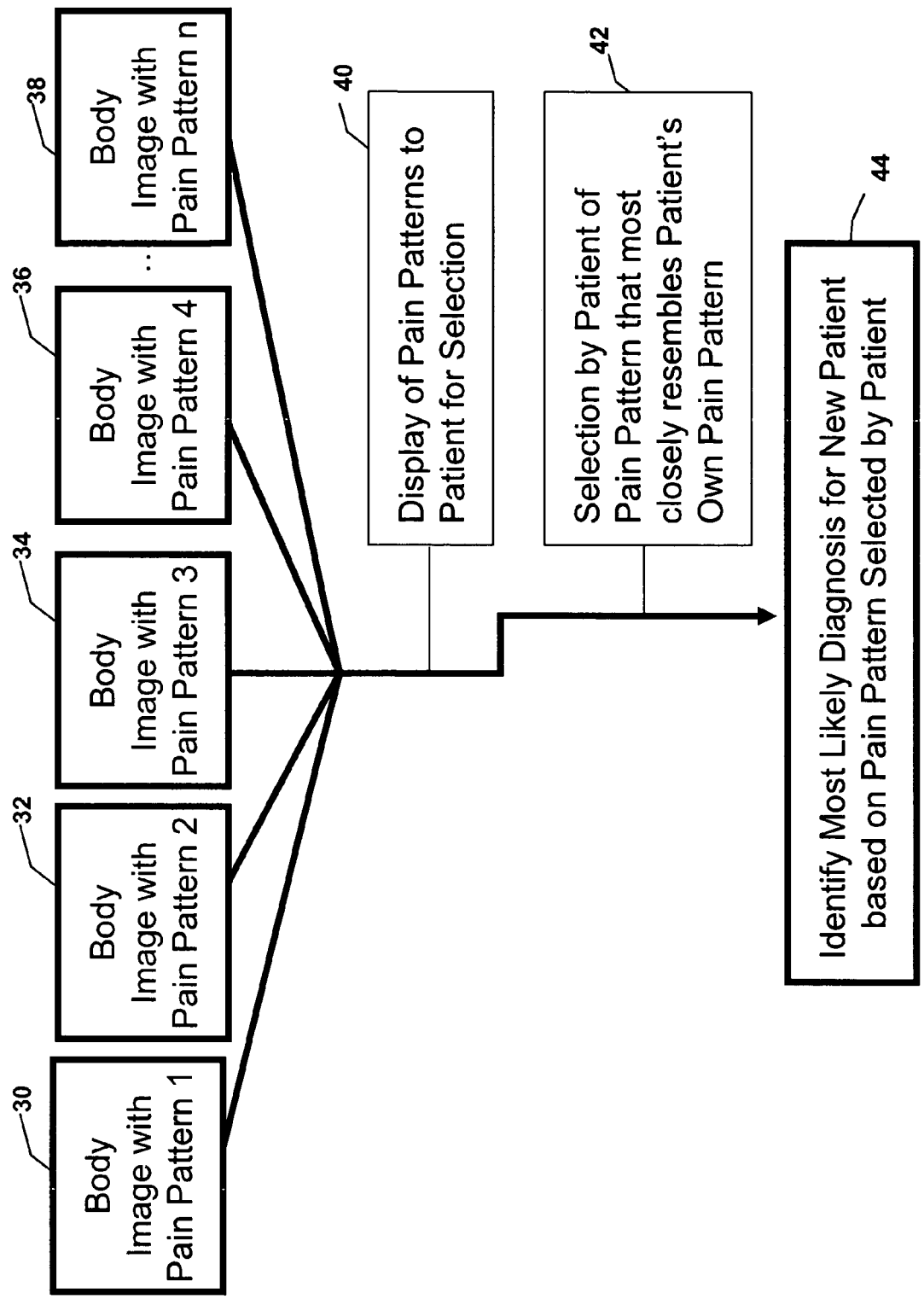
FIG. 4 is a flow chart in which possible diagnoses are obtained by the patient selecting from multiple pre-selected pain locations.

FIG. 4 is a flow chart in which multiple pre-selected pain locations 30, 32, 34, 36, 38 suggesting particular diagnoses are displayed 40 to a patient with pain, so that the patient may select 42 that pain pattern which most closely resembles the patient's own pain pattern so as to identify 44 the most likely diagnosis.

Figure 5:
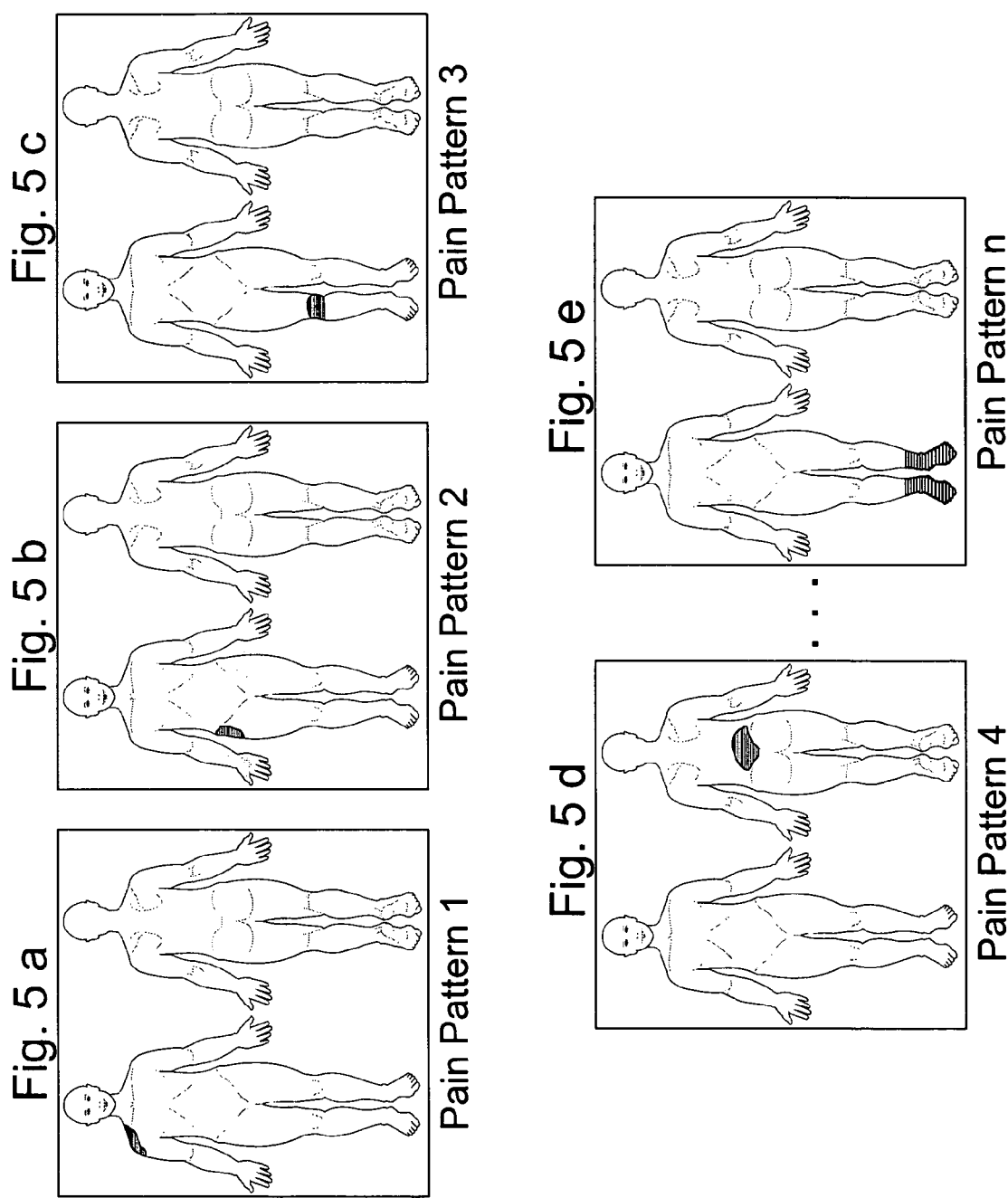
FIGS. 5 a-e shows examples of body images, used in the process described in FIG. 4.

FIGS. 5 a-e shows examples of body images, used in the process described in FIG. 4, showing pre-selected patterns of pain location of the shoulder (FIG. 5 a), hip (FIG. 5 b), knee (FIG. 5 c), lower back (FIG. 5 d), and the bilateral pain in the foot and lower leg typical of peripheral neuropathy (FIG. 5 e).

Figure 6:
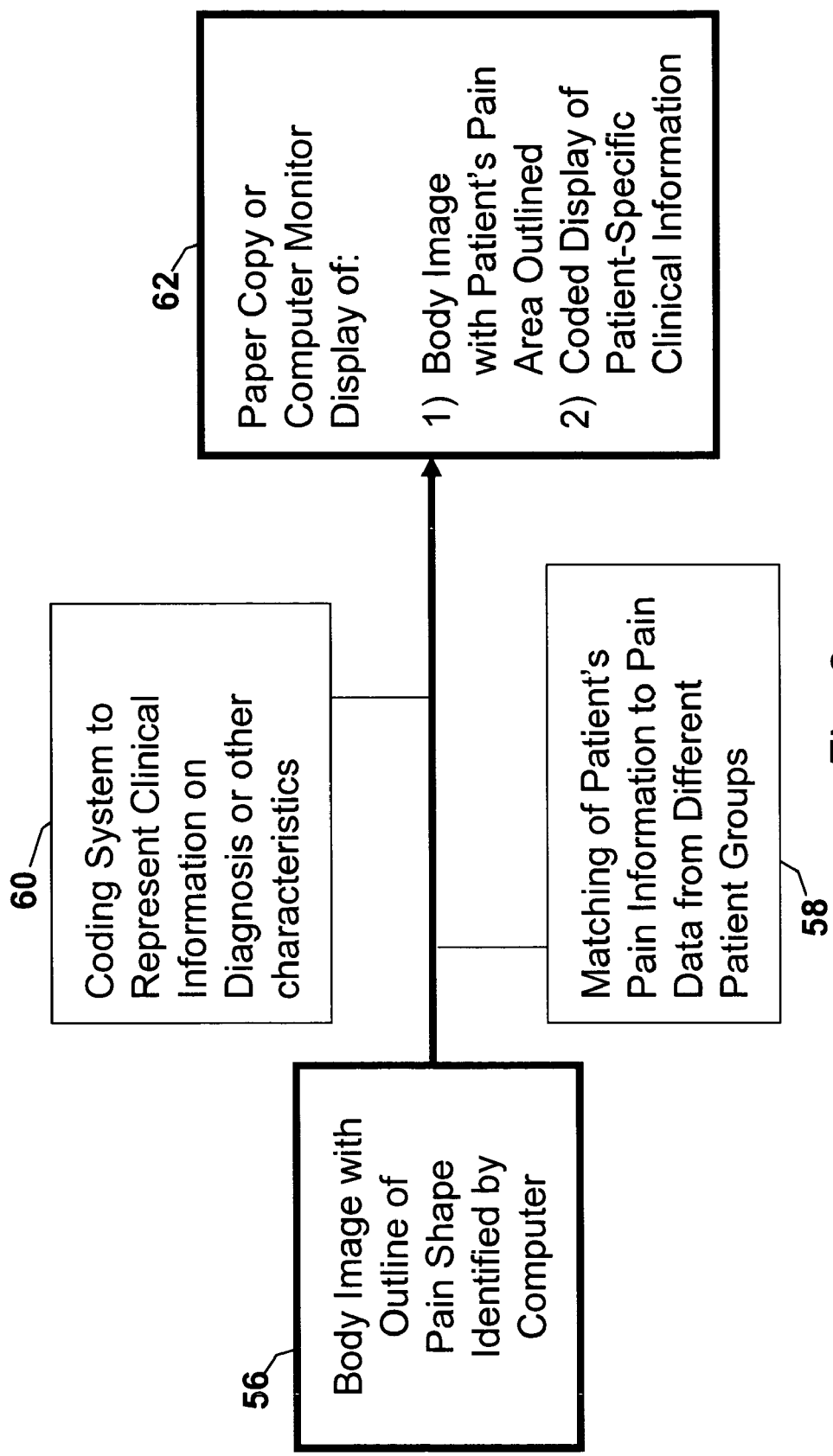
FIG. 6 is a flow chart in which a visual display is generated by computer to display a pain outline for an actual patient together with coded displays of related clinical information.

FIG. 6 is a flow chart in which a human body image 56 containing a computer-identified pain shape is compared 58 with pain data from different patient groups and, using a coding system to represent different types of clinical information 60, a visual display 62 is generated by computer to display a pain outline for an actual patient together with coded displays of related clinical information.

Figure 7:
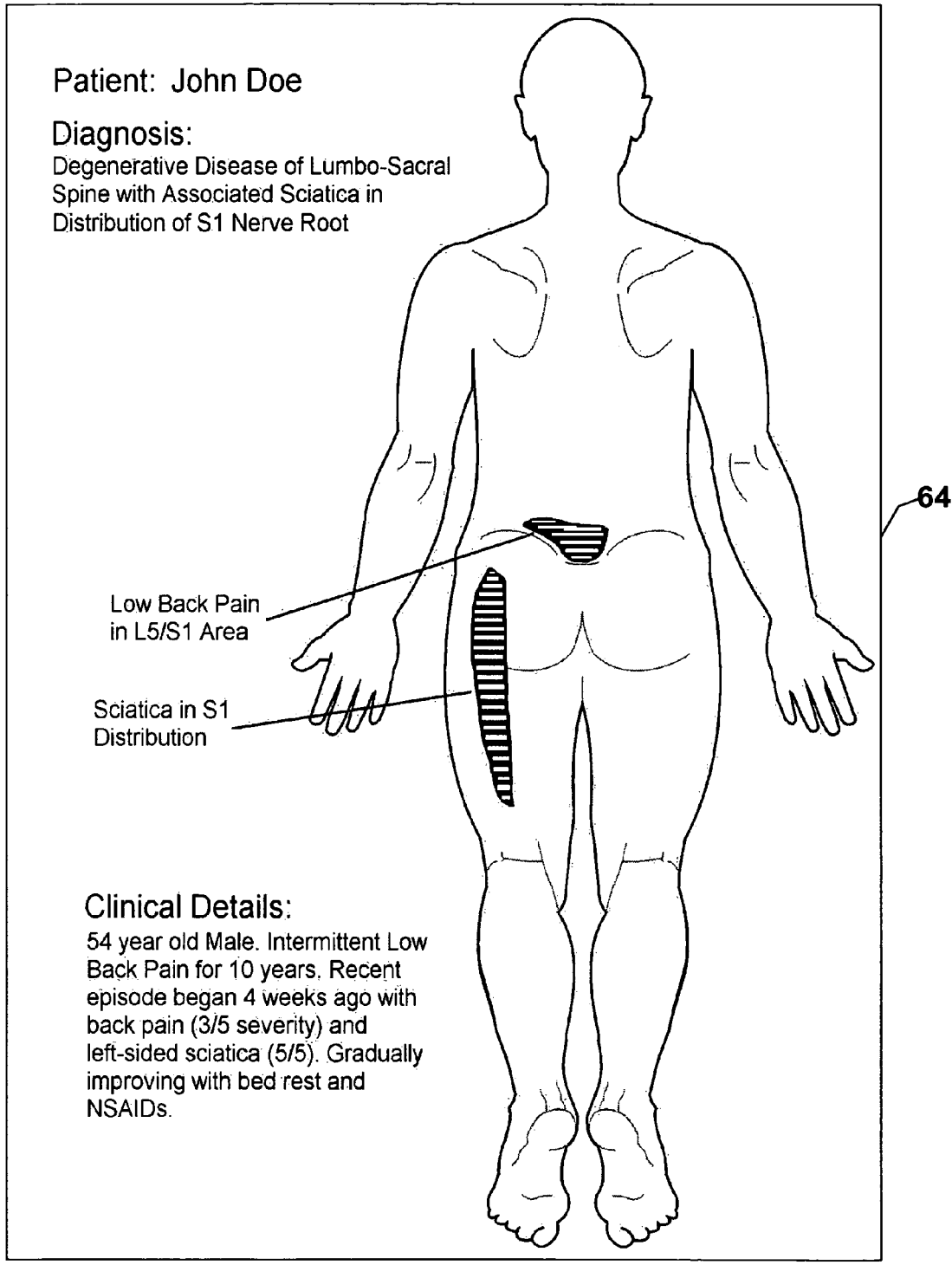
FIG. 7 shows an example of a visual display generated according to the process in FIG. 6.

FIG. 7 shows an example of a visual display 64 generated according to the process in FIG. 6 in which lower back pain and sciatica pain shapes are displayed and associated with related textual clinical information.

Figure 8:
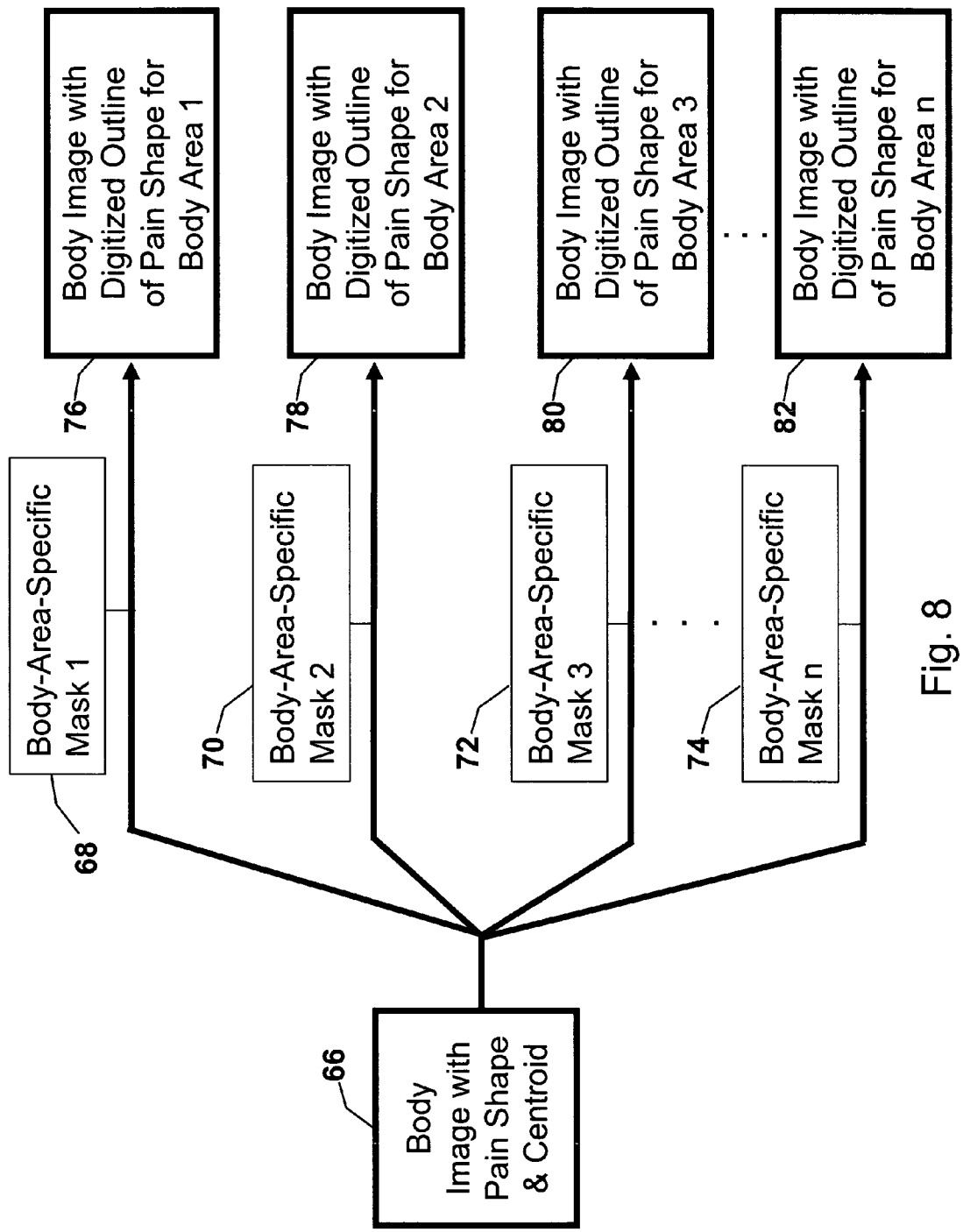
FIG. 8 is a flow chart in which body-area-specific masks are used to allocate pain shapes to specific body areas based on the location of the pain shape centroids.

FIG. 8 is a flow chart in which a human body image 66 with a computer-generated pain shape and calculated centroid is analyzed using a sequence of body-area-specific masks 68, 70, 72, 74 to identify if the centroid is located inside the particular body-area-specific mask. If so, the computer-generated pain shape is recorded as being associated with the specific body area 76, 78, 80, 82.

Figure 9:
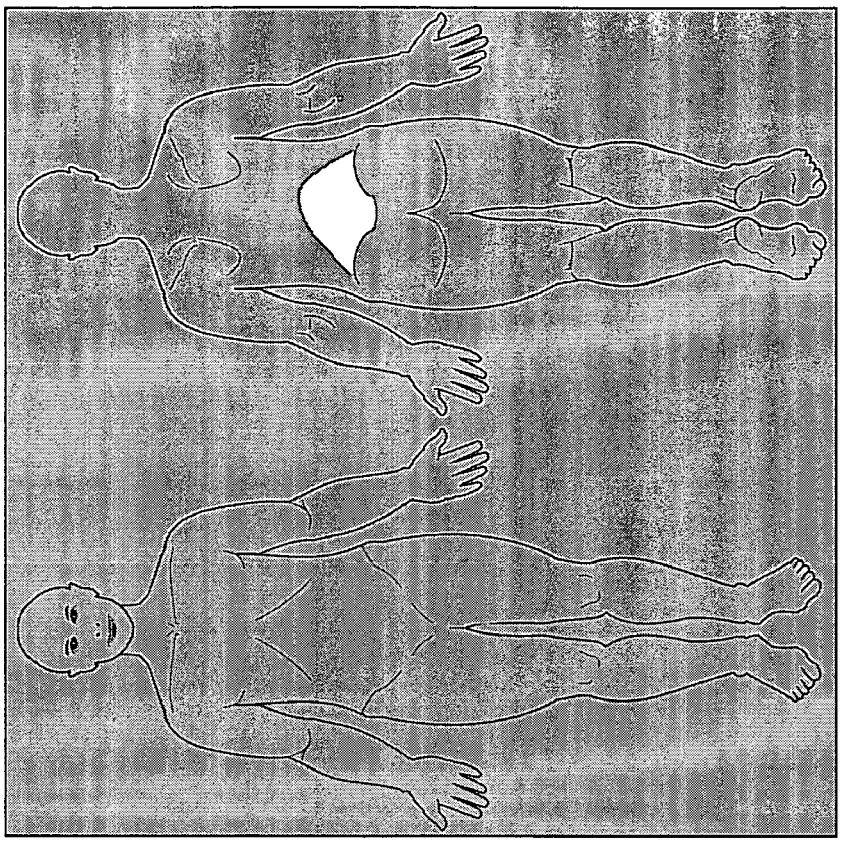
FIGS. 9 a and 9 b show examples of body-area-specific masks used in the process described in FIG. 8.
Figure 9:
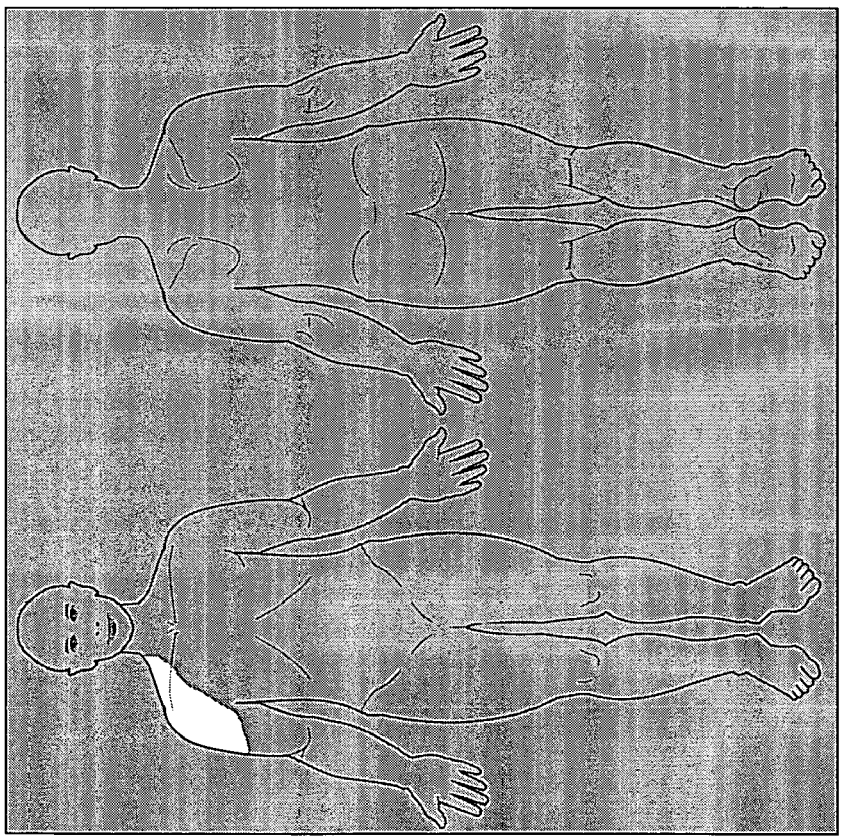

FIGS. 9a and 9b show examples of body-area-specific masks for the right anterior shoulder (FIG. 9a), and for the lower back (FIG. 9b), as used in the process described in FIG. 8. The specific outline of a body-area-specific mask is dependent on the spatial distribution of the centroids for the pain shapes for the patients with pain in the specific body area. Thus, the lower back mask shown in FIG. 9b is not bilaterally symmetrical and reflects the greater frequency of right-sided back pain (and of right-sided sciatica) in a lower back pain population.

Figure 10:
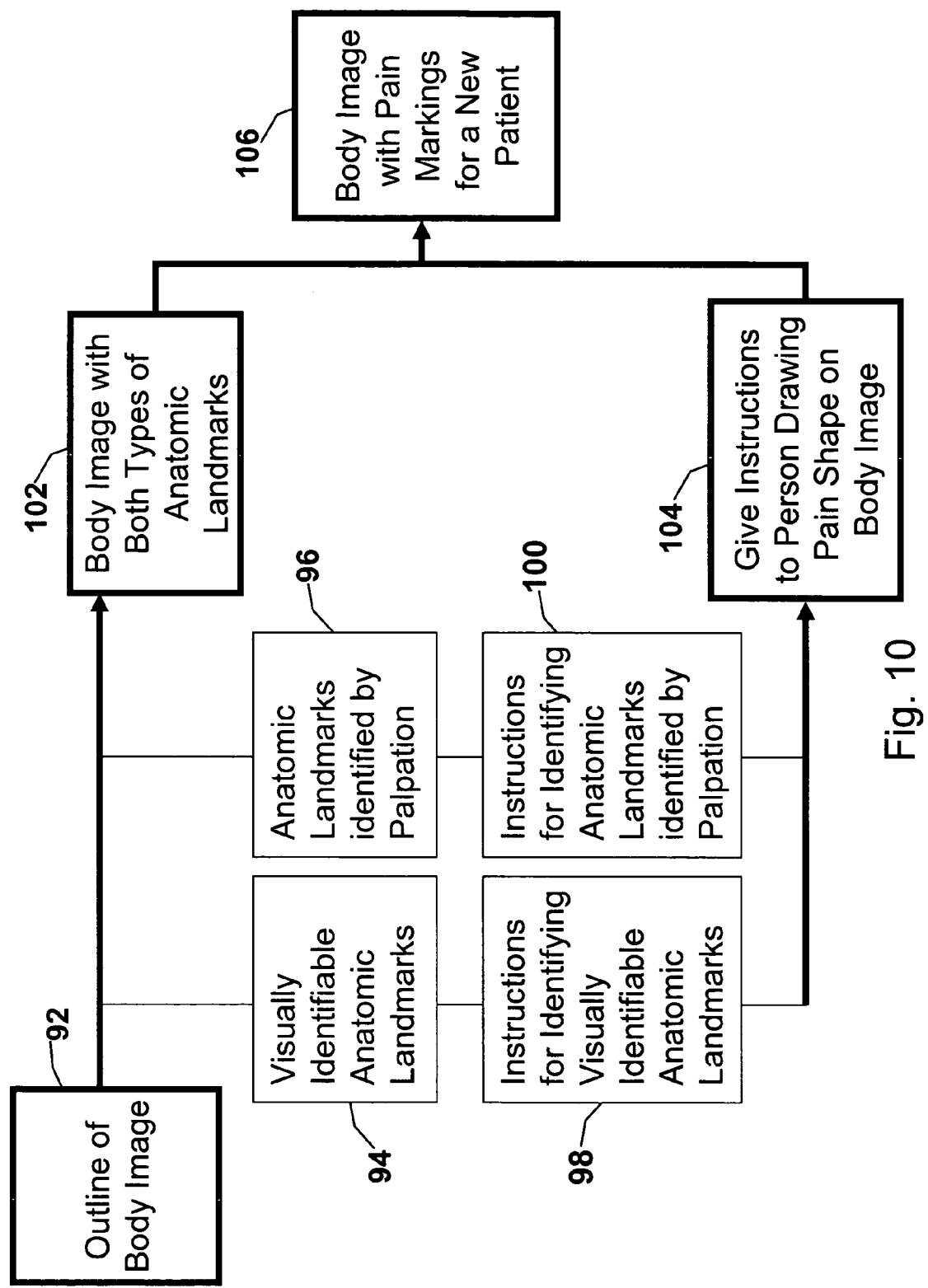
FIG. 10 is a flow chart in which anatomic landmarks are added to a human body image and associated with instructions for identifying such landmarks.

FIG. 10 is a flow chart in which an unmarked human body image 92 is edited 94, 96 to add visually identifiable anatomic landmarks and anatomic landmarks detected by body palpation resulting in a revised human body image 102 containing both types of anatomic landmarks. Instructions 98, 100 as to how to identify these landmarks are given 104 to the person making the pain markings for a patient, resulting in a body image 106 containing pain markings in accordance with these instructions. In obese patients, a landmark that is visible in a thin person may not visible, requiring palpation rather than visual identification.

Figure 11:
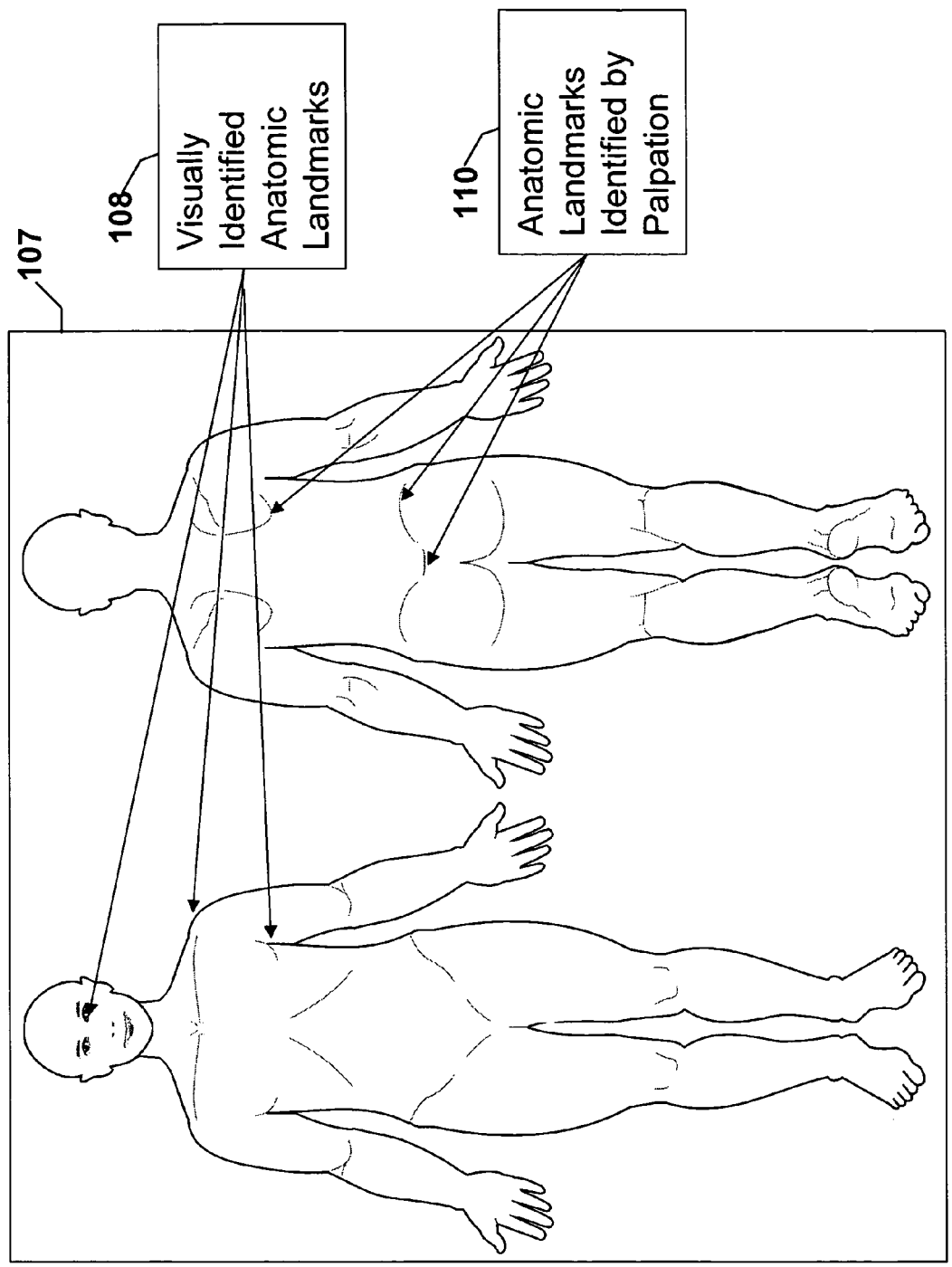
FIG. 11 shows examples of anatomic landmarks identified in accordance with the process described in FIG. 10.

FIG. 11 shows examples of anatomic landmarks identified by visual inspection 108 or by palpation of the body 110 in accordance with the process described in FIG. 10.

Figure 12:
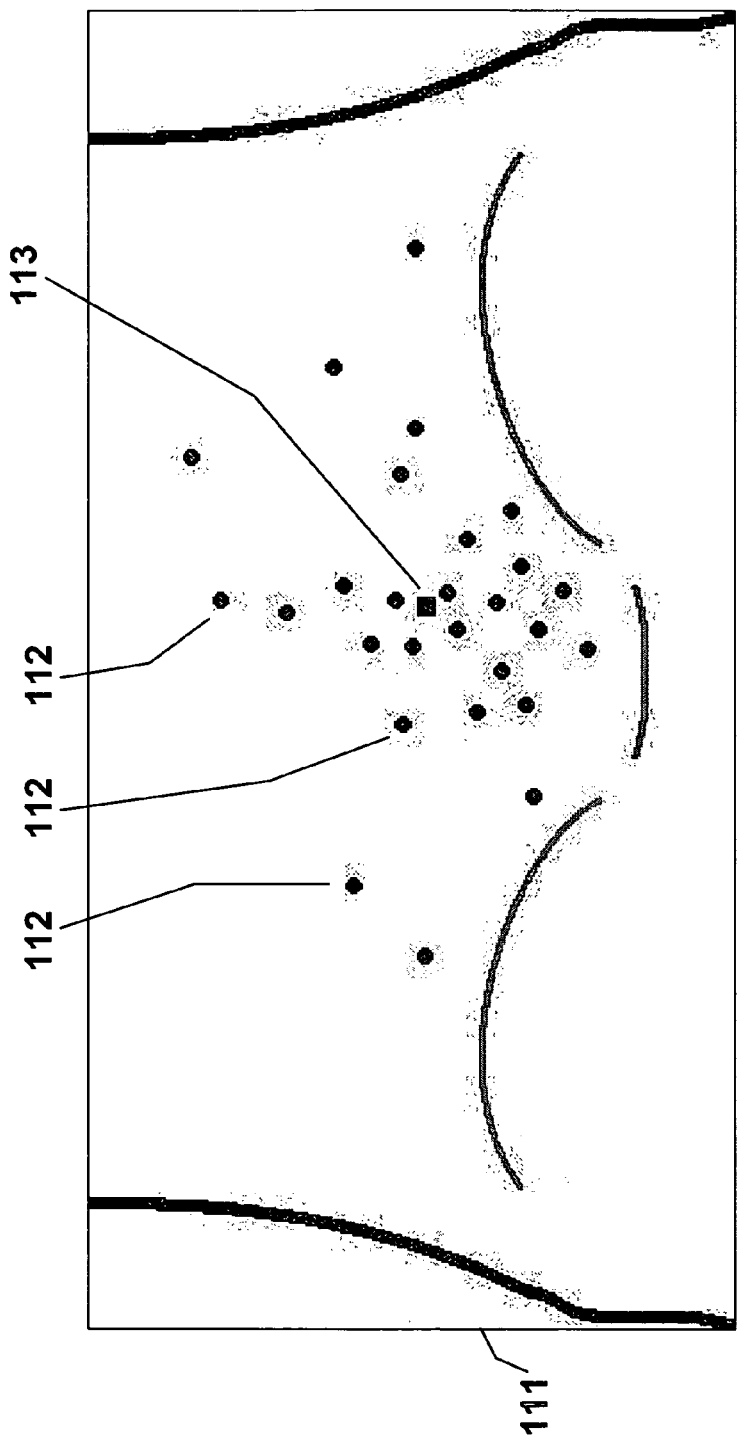
FIG. 12 shows a human body image in which centroids are used as markers of pain location. The meta-centroid for the centroids is also displayed.

FIG. 12 shows a human body image 111 in which a set of centroids 112 for different pain shapes are displayed, together with a meta-centroid 113 reflecting the center of the set of centroids 112. The centroid serves as a stable marker of the position of a given pain shape. The meta-centroid 113 serves as a stable marker of the center of a group of pain shapes.

Figure 13:
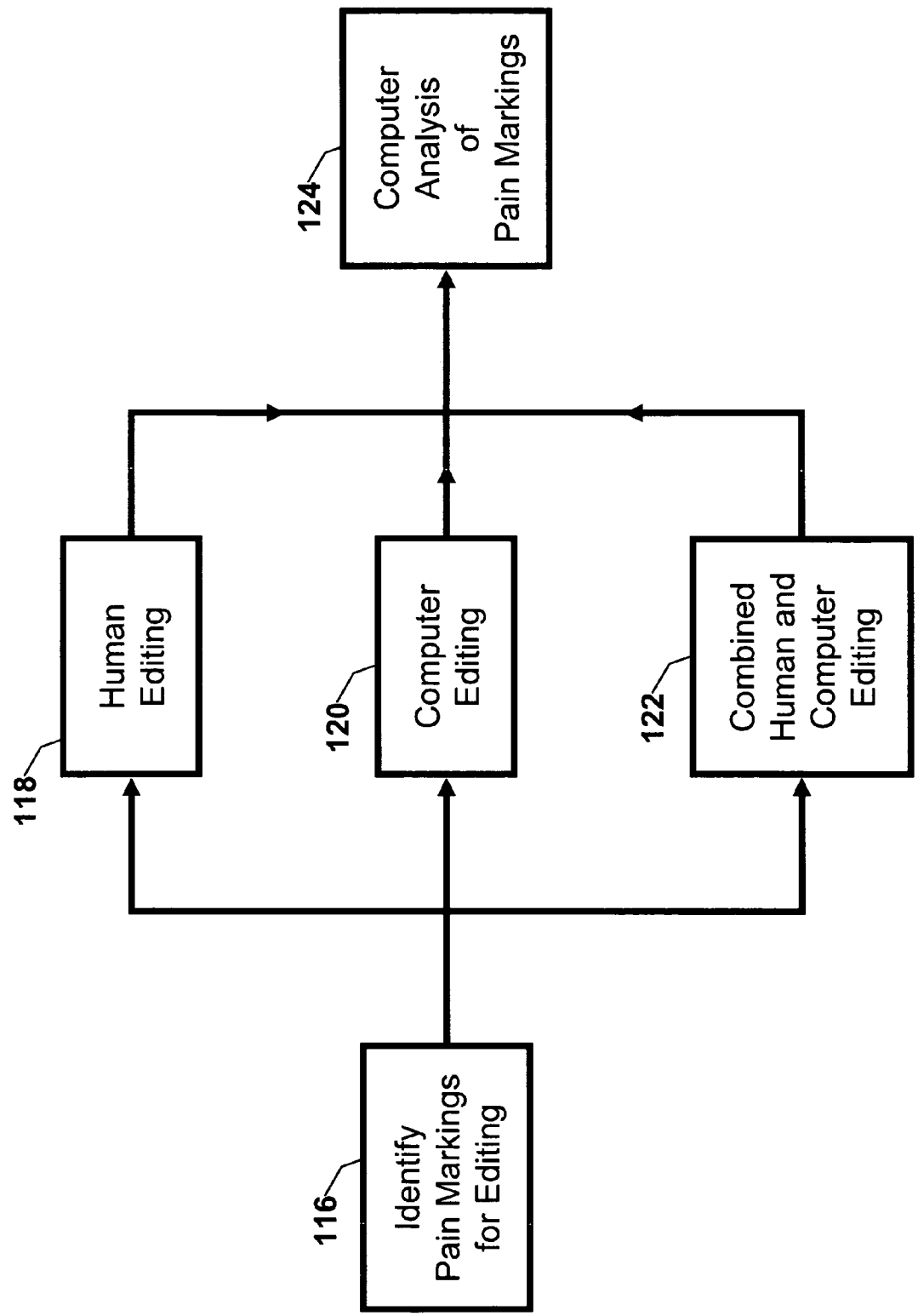
FIG. 13 is a flow chart in which pain markings of sub-optimal quality are edited so as to provide good quality pain markings for computer analysis.

FIG. 13 is a flow chart in which pain markings of sub-optimal quality are identified for editing 116, followed by human editing 118, computer editing 120 or combined human and computer editing 122. Computer analysis of pain markings 124 is then performed to identify pain markings of adequate quality for subsequent computer identification of pain shape outlines.

Figure 14A:
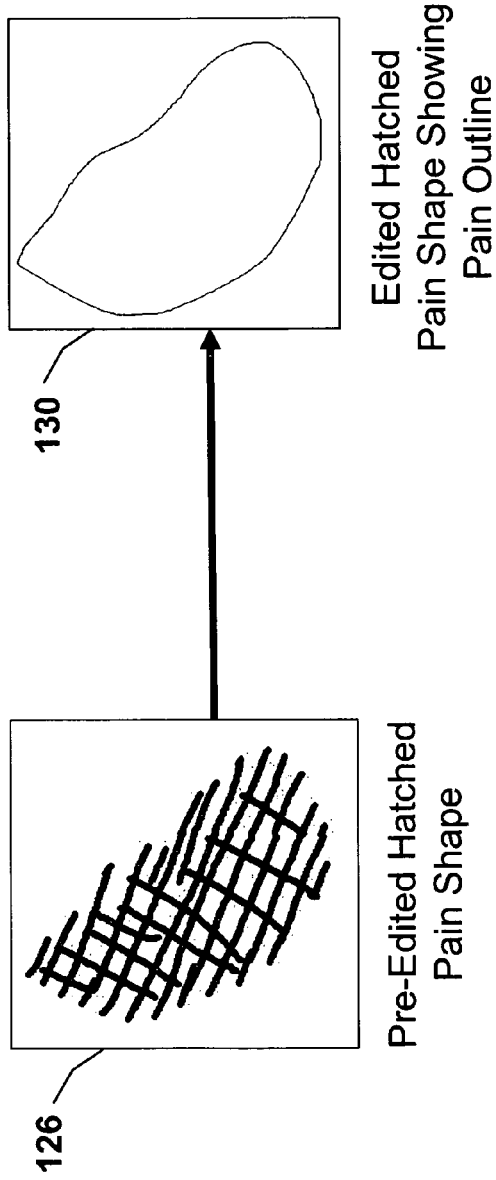
FIGS. 14 a and 14 b show two examples of sub-optimal pain markings that may be converted to good quality pain markings in accordance with the process in FIG. 13.
Figure 14B:
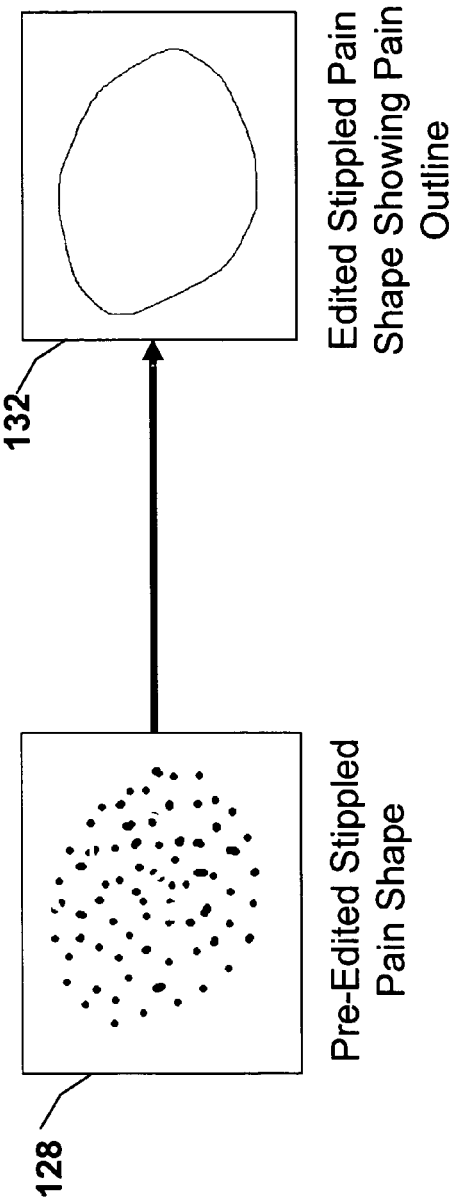

FIGS. 14a and 14b show two examples of sub-optimal pain markings. FIG. 14a shows a hatched pain shape 126 that may be converted to good quality pain markings 130 for pain outline identification. FIG. 14b shows a stippled pain shape 128 that may be converted to good quality pain markings 132 for pain outline identification.

Figure 15:
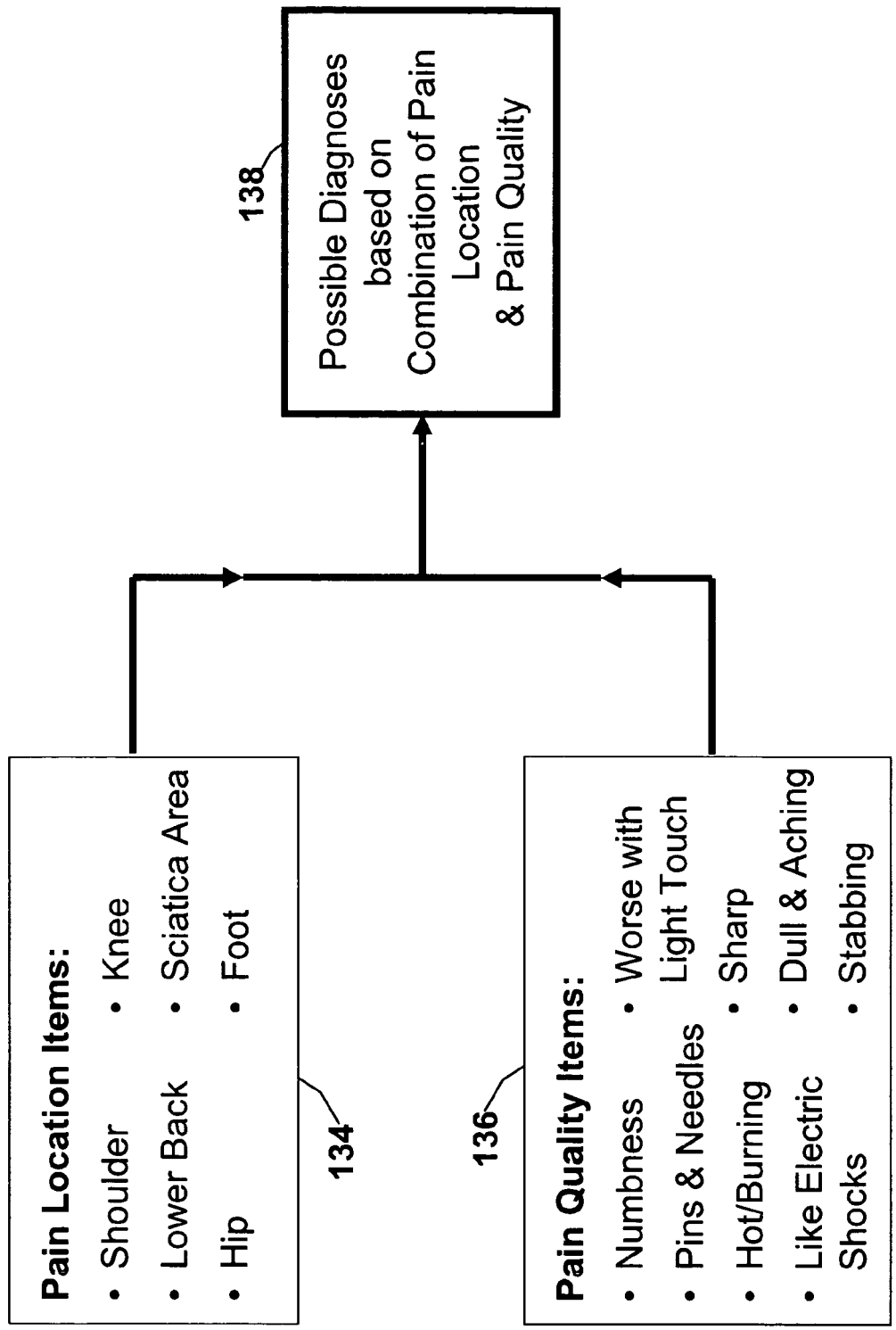
FIG. 15 is a flow chart in which pain location and pain quality variables are combined to provide improved diagnostic precision.

FIG. 15 is a flow chart in which a set of clinical variables related to pain location 134 are combined with a set of clinical variables related to pain quality 136, resulting in greater diagnostic precision than is obtained by either set of variables alone 138.

Figure 16:
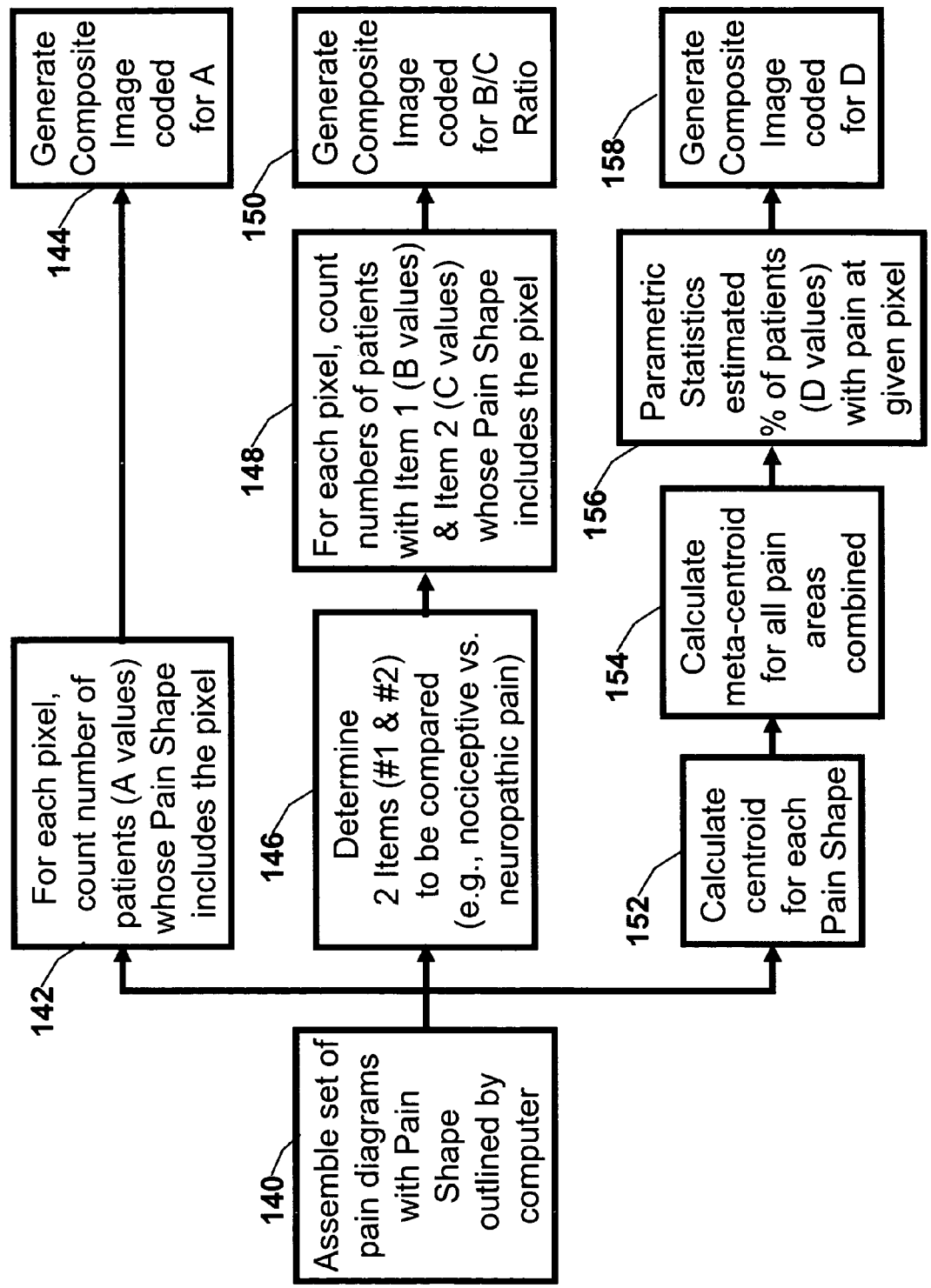
FIG. 16 is a flow chart illustrating the process of generating composite images of three types from a set of individual pain outlines.

FIG. 16 is a flow chart in which a set of body image designs with computer-identified pain shapes 140 is used to generate three types of composite image. For the first type, the number of patients whose pain shape includes a given pixel is determined 142 and a composite image reflecting these values produced 144. For the second type, two clinical pain features are selected 146; then the number of patients whose pain shape shows one clinical pain feature is determined as well as the number of patients whose pain shape shows the other clinical pain feature 148; then a composite image reflecting the ratio of these values is produced 150. For the third type, a centroid is calculated for each pain shape 152, a meta-centroid is calculated for all pain shapes combined 154, radial distances from the meta-centroid and parametric statistics are used to determine the estimated percentage of patients with pain at a given pixel 156, and a composite image reflecting these values (e.g., a pain outline encompassing a predicted percentage of patient outlines) is produced 158.

Figure 17:
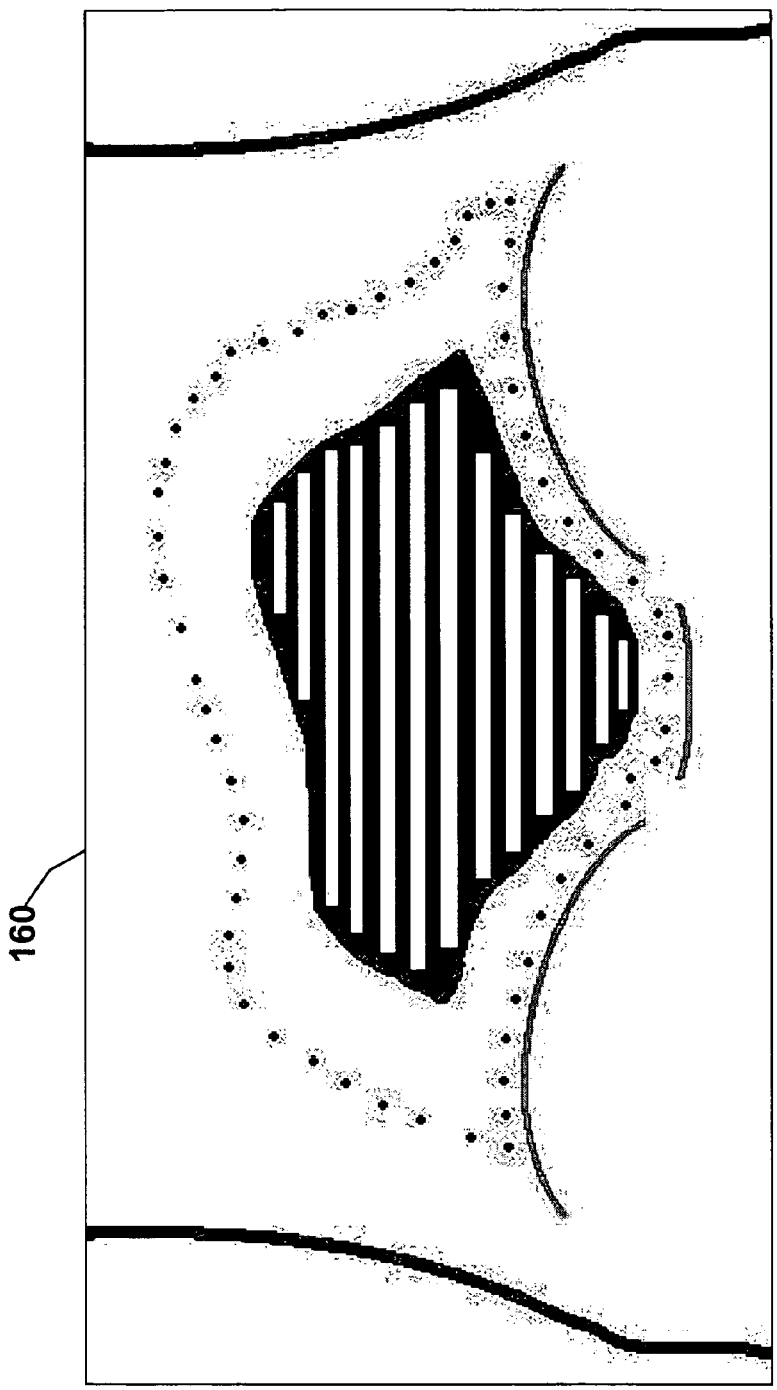
FIG. 17 shows an example of one type of composite image generated using the process in FIG. 16.

FIG. 17 shows an example of the third type of composite image 160 described in FIG. 16. This example shows the estimated probability of a given outline of an individual pain shape in the lower back lying inside two perimeters—the perimeter of the black central area representing approximately 50% of outlines, and the outer dotted line perimeter encompassing approximately 80% of outlines.

Figure 18:
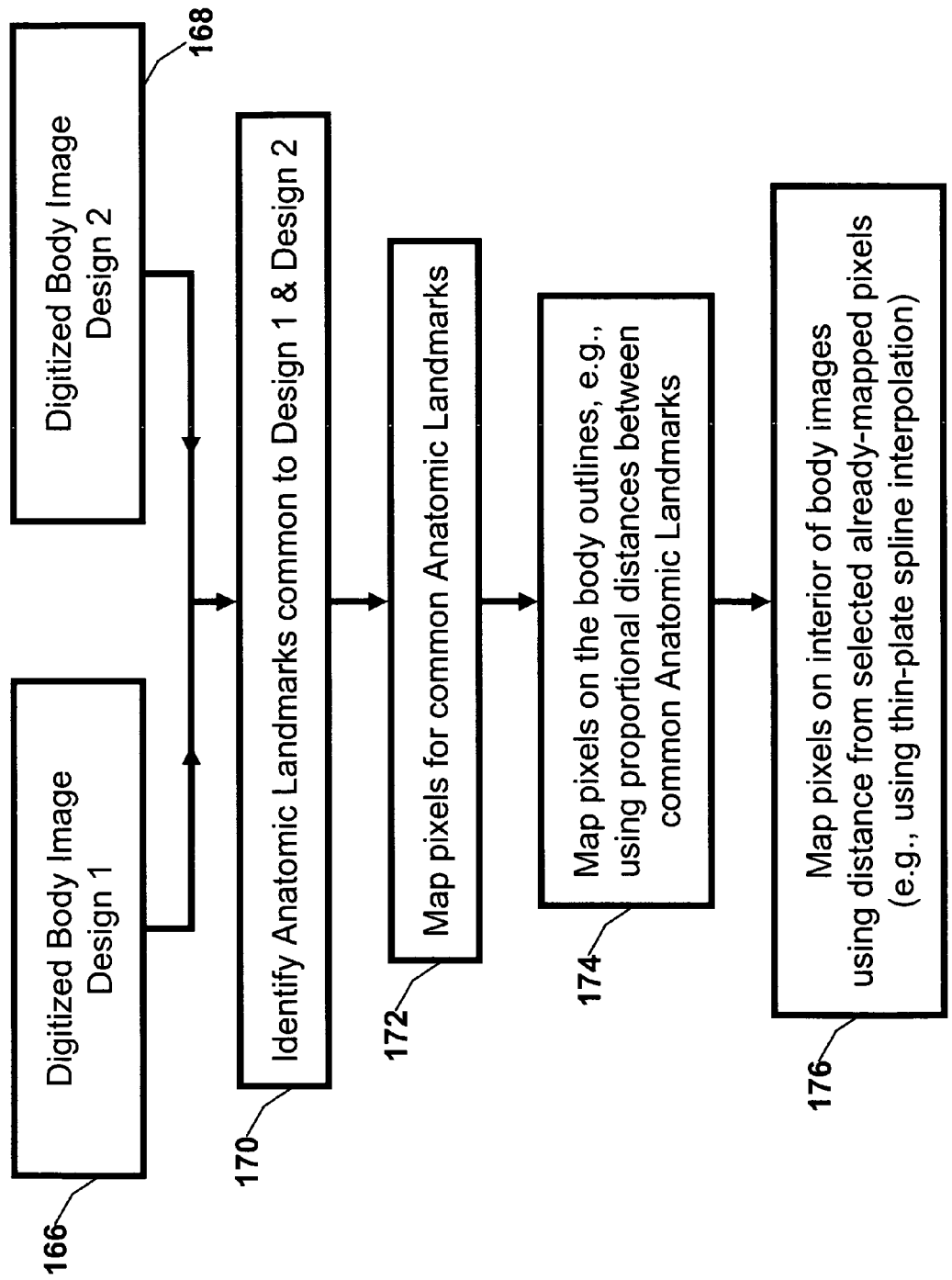
FIG. 18 is a flow chart in accordance with the invention in which individual pixels in two separate human body image designs are mapped to each other, allowing transfer of pain data recorded in one image to comparable locations in the other image.

FIG. 18 is a flow chart for mapping the pixels in two different human body image designs 166, 168. The first step 170 is to identify anatomic landmarks common to the two designs. The second step 172 is to map the pixels for these landmarks from one image to the other. The third step 174 is to map the pixels lying along the body outlines from one image to the other (for example, using proportional distances between common anatomic landmarks along the outline or using the sliding semilandmark method). The final step 176 is to map the pixels lying on the interior of the body outlines from one image to the other, using selected mapped pixels derived from 172 and 174 together with warped spaces derived from techniques such as thin-plate spline interpolation.

Figure 19:
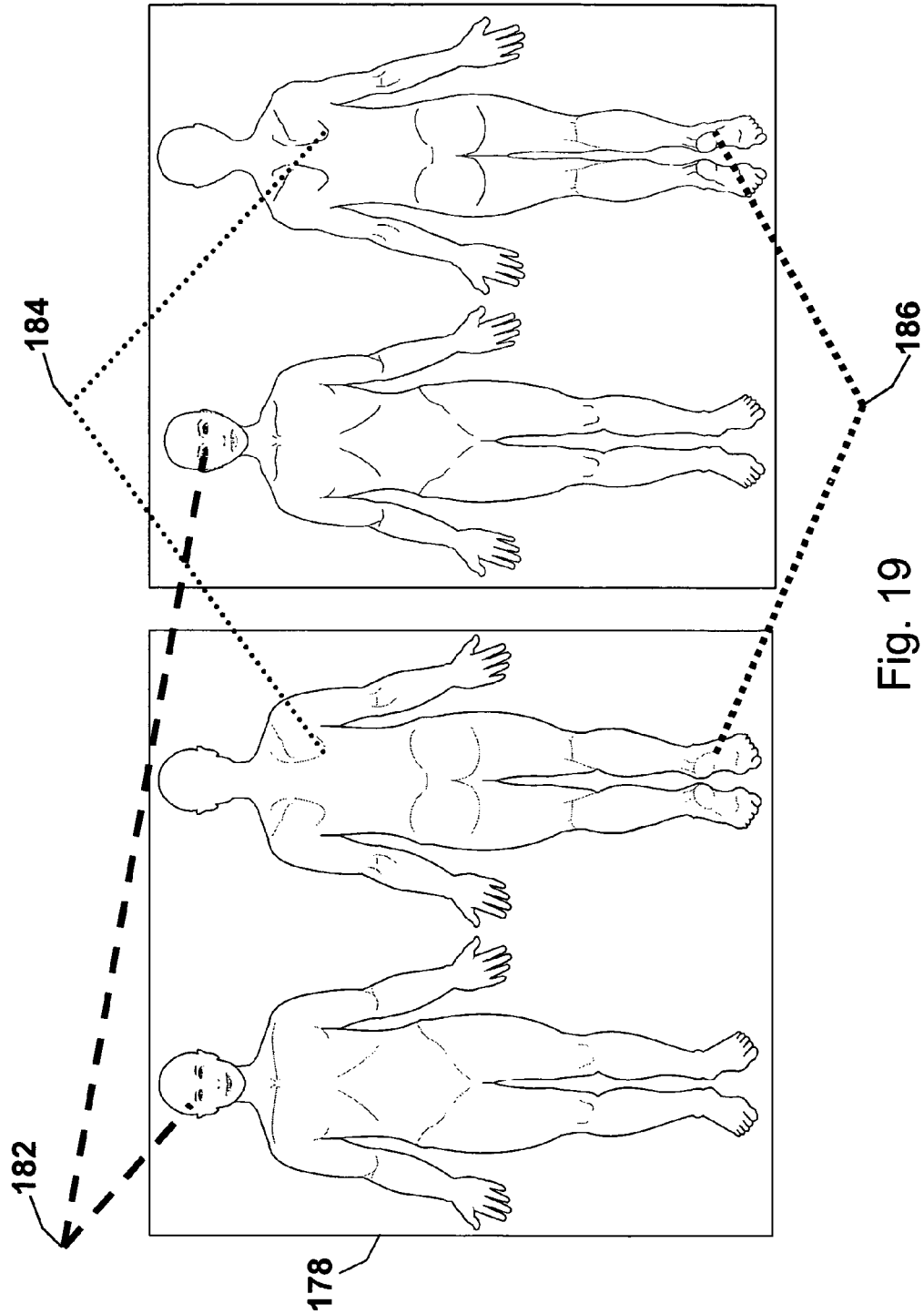
FIG. 19 shows examples of anatomic landmarks used as a basis for the mapping process described in FIG. 18.

FIG. 19 shows two human body images 178 of different design, and three examples of paired anatomic landmarks (for the right eye 182, the lower end of the scapula 184 and the plantar fascia 186) used as a basis for the mapping process described in FIG. 18.

FIGS. 20a-o show examples of the many different human body image designs used in the evaluation of pain, indicating the need for the process required in FIG. 18.

It is clear that the interactions between the various components of the methods of the present invention follow well known clinical and computer principles and techniques, and need not be further described in order to avoid unnecessarily complicating the drawings and specification. Thus, the computer may be an IBM™PC-compatible personal computer using an Intel microprocessor of the Pentium or later CPU series and running the Microsoft Windows™ operating environment.

Those skilled in the art will recognize that users may employ somewhat different image types, analytical approaches, computer hardware or computer software, all of which are supported by the present invention.

There has been disclosed heretofore the best embodiments of the invention presently contemplated. However, it is to be understood that various changes and modifications may be made thereto without departing from the spirit and scope of the present invention.

What is claimed is:

1. A method for identifying clinical characteristics of a patient's pain, comprising the steps of:
   a. providing a first human body image without pain indicia recorded thereon;
   b. providing a second human body image substantially similar to said first human body image other than having recorded thereon readable indicia of a first patient's pain, said indicia being recorded on said second human body image at locations in correspondence with locations of the first patient's actual pain;
   c. digitizing said first human body image and said second human body image if not already digitized;
   d. coregistering said first human body image and said second human body image;
   e. comparing electronically said first human body image and said second human body image to determine at least one set of contiguous electronic locations of said pain indicia;
   f. calculating a single point centroid based on locations of actual pain, said actual pain locations comprising a pain shape;
   g 1. using said single point centroid to allocate said pain shape to a given human body location;
   g 2. producing a database of said pain centroids for a plurality of patients known to belong to at least one clinical group identified by at least one of a diagnostic category or a disease severity category;
   h. comparing the first patient's pain centroid with said database; and
   i. judging based on said comparison if the first patient is included in at least one of said clinical groups.

2. A method as in claim 1 wherein said second human body image is created using a digitized version of said first human body image, said first human body image being electronically displayed for electronic recording of said pain indicia by a user.

3. A method as in claim 1, further comprising:
   i. determining a pain shape determined by the outline of said set of contiguous electronic locations, wherein a pain shape for the first patient is matched with at least one pain shape pattern characteristic of said at least one clinical group, and comprising the further steps of:
      repeating steps a—g2 and i on a plurality of patients in said at least one clinical group to create a respective first visual display derived from pain shapes characteristic of said clinical group;
      providing a first copy of said first human body image to which said first visual display is added;
      reviewing the first patient's copy of step b; and
      identifying if said first visual display, characteristic of said at least one clinical group, corresponds to the location of pain provided by the first patient in step b.

4. A method as in claim 3 wherein a visual display of a pain shape is combined with other coded clinical information, comprising the further steps of:
   determining a coding system for a second visual display of clinical information related to said pain shape and the first patient;
   drawing by computer on a second copy of said digitized first human body image said pain shape for the first patient; and
   drawing by computer on said second copy said second visual display that is visually linked to said pain shape for the first patient, whereby all relevant clinical information is combined in a single integrated display.

5. A method as in claim 3 wherein composite images are generated for a plurality of patients, comprising the steps of:
   determining body locations of a plurality of said pain shapes;
   determining a coding system of visual markers to provide information on said body locations of said pain shapes; and
   providing a composite image in which said visual markers are added to a fourth copy of said first human body image so as to indicate the overall body location distribution of said pain shapes.

6. A method as in claim 5 wherein a smoothing of the composite image is obtained using parametric statistics, comprising the steps of:
   calculating a meta-centroid for said pain shapes;
   calculating a distance between said meta-centroid and the outline of each said pain shape along each radial from the meta-centroid outwards in one direction, disregarding both that portion of said outline that is on the other side of the meta-centroid and that portion of said outline that is the inner portion of the outline for an outline that does not encompass the meta-centroid;
   calculating parametric statistics for said pain shapes for the aggregate of said distances for each said radial; and
   providing a visual display on a fifth copy of said first human body image that shows the statistical likelihood, on the basis of parametric statistics, of a said pain shape occupying a given pixel at a given distance from the meta-centroid.

7. A method as in claim 3, wherein body-area-specific masks are used to focus body image analysis on particular body locations, comprising the further steps of:
   providing at least one digitally marked body area on a third copy of said first human body image;
   comparing said digitally marked body area and said centroid position and categorizing said pain shape as a member of the class of pains in said body area if said centroid lies inside said digitally marked body area.

8. A method as in claim 3, wherein said coregistering is achieved using anatomic landmarks identified by visual inspection of a human body and also landmarks that are identified only by palpation of a human body, comprising the further steps of:
   providing said first human body image having both visual and palpable types of anatomic landmarks; and
   visually displaying a coding system containing instructions for identification of at least one said anatomic landmark.

9. A method as in claim 3, wherein differentiation between said first human body image and said second human body image is obtained by using different colors that can be separately identified by computer, comprising the further steps of:

producing a said first human body image in which the body outline and other anatomic markings are printed in a first color that has a low value for at least one of three constituent RGB colors that is easily visible to a human being;

recording said readable indicia on said second human body image using a marking device that produces markings in a second color that has a greater value than with the first color for at least one of said constituent RGB colors;

producing a computer-readable color digitized version of said second human body image; and producing a digitized image confined to said readable indicia by having said computer select pixels for analysis based on differences in values between said constituent RGB colors in said color digitized version.

10. A method as in claim 3, wherein said pain indicia that have been improperly recorded are edited prior to identification of said electronic locations, comprising the further steps of:

analyzing said pain indicia on said second human body image to identify non-contiguous pain indicia in which all pixels are not contiguous;

identifying which of said non-contiguous pain indicia may properly be considered editable pain indicia; and incorporating intervening pixels between said editable pain indicia with said editable pain indicia so as to form a single pain indicia object containing a contiguous set of pixels.

11. A method as in claim 1 wherein body-area-specific masks are used to focus body image analysis on particular body locations, comprising the further steps of:

providing at least one digitally marked body area on a third copy of said first human body image;

comparing said digitally marked body area and said centroid position and categorizing said pain shape as a member of the class of pains in said body area if said centroid lies inside said digitally marked body area.

12. A method as in claim 1 wherein said coregistering is achieved using anatomic landmarks identified by visual inspection of a human body and also landmarks that are identified only by palpation of a human body, comprising the further steps of:

providing said first human body image having both visual and palpable types of anatomic landmarks; and visually displaying a coding system containing instructions for identification of at least one said anatomic landmark.

13. A method as in claim 1 wherein differentiation between said first human body image and said second human body image is obtained by using different colors that can be separately identified by computer, comprising the further steps of:

producing a said first human body image in which the body outline and other anatomic markings are printed in a first color that has a low value for at least one of three constituent RGB colors that is easily visible to a human being;

recording said readable indicia on said second human body image using a marking device that produces markings in a second color that has a greater value than with the first color for at least one of said constituent RGB colors;

producing a computer-readable color digitized version of said second human body image; and producing a digitized image, confined to said readable indicia by having said computer select pixels for analysis based on differences in values between said constituent RGB colors in, said color digitized version.

14. A method as in claim 1 wherein said pain indicia that have been improperly recorded are edited prior to identification of said electronic locations comprising the further steps of:

analyzing said pain indicia on said second human body image to identify non-contiguous pain indicia in which all pixels are not contiguous;

identifying which of said non-contiguous pain indicia may properly be considered editable pain indicia; and incorporating intervening pixels between said editable pain indicia with said editable pain, indicia so as to form, a single pain indicia object containing a contiguous set of pixels.

15. A method as in claim 1 wherein step h is performed by incorporating information on both pain location and pain quality.

16. A method as in claim 1 wherein human body image and said second human body image are based on a photograph of the first patient.

* * * * *